US012167853B2

(12) United States Patent
MacEwan et al.

(10) Patent No.: US 12,167,853 B2
(45) Date of Patent: Dec. 17, 2024

(54) NON-WOVEN GRAFT MATERIALS FOR NERVE REPAIR AND REGENERATION

(71) Applicant: Acera Surgical, Inc., St. Louis, MO (US)

(72) Inventors: Matthew R. MacEwan, St. Louis, MO (US); Lily Jeng, St. Louis, MO (US); Abdolrasol Rahimi, St. Louis, MO (US); Manisha Jassal, West Warwick, RI (US); Tamas Kovacs, St. Louis, MO (US)

(73) Assignee: Acera Surgical, Inc., St. Louis, MO (US)

( * ) Notice: Subject to any disclaimer, the term of this patent is extended or adjusted under 35 U.S.C. 154(b) by 0 days.

(21) Appl. No.: 17/903,918

(22) Filed: Sep. 6, 2022

(65) Prior Publication Data

US 2023/0074964 A1 Mar. 9, 2023

Related U.S. Application Data

(60) Provisional application No. 63/241,366, filed on Sep. 7, 2021.

(51) Int. Cl.
| *A61B 17/11* | (2006.01) |
| *A61L 27/18* | (2006.01) |
| *A61L 27/22* | (2006.01) |
| *A61L 27/24* | (2006.01) |
| *A61L 27/54* | (2006.01) |

(Continued)

(52) U.S. Cl.
CPC .......... *A61B 17/1128* (2013.01); *A61L 27/18* (2013.01); *A61L 27/225* (2013.01); *A61L 27/24* (2013.01); *A61L 27/54* (2013.01); *A61L 27/56* (2013.01); *A61L 27/58* (2013.01); *A61L 2300/412* (2013.01); *A61L 2300/604* (2013.01); *A61L 2430/32* (2013.01)

(58) Field of Classification Search
CPC ............ A61B 17/1128; A61L 2430/32; A61L 2430/03
See application file for complete search history.

(56) References Cited

U.S. PATENT DOCUMENTS

| 2,068,703 A | 1/1937 | Powdermaker |
| 3,280,229 A | 10/1966 | Simons |

(Continued)

FOREIGN PATENT DOCUMENTS

| AU | 2011268321 | 1/2013 |
| AU | 2012390291 | 9/2017 |

(Continued)

OTHER PUBLICATIONS

Hoke, Nanofiber Nerve Guide for Peripheral Nerve Repair and Regeneration, US Army Medical Research and Material Command. ( Year: 2014).*

(Continued)

*Primary Examiner* — Carlos A Azpuru
(74) *Attorney, Agent, or Firm* — VIA LLP

(57) ABSTRACT

Disclosed herein are non-woven graft materials for use in specialized surgical procedures involving nerve repair and regeneration. Some embodiments describe electrospun fiber products such as conduits, wraps, or grafts comprising a resorbable hybrid-scale matrix to facilitate nerve repair and regeneration.

54 Claims, 2 Drawing Sheets

(51) Int. Cl.
*A61L 27/56* (2006.01)
*A61L 27/58* (2006.01)

(56) References Cited

U.S. PATENT DOCUMENTS

| | | |
|---|---|---|
| 3,338,992 A | 8/1967 | Kinney |
| 3,341,394 A | 9/1967 | Kinney |
| 3,502,763 A | 3/1970 | Hartmann |
| 3,542,615 A | 11/1970 | Dobo et al. |
| 3,692,618 A | 9/1972 | Dorschner et al. |
| 3,740,302 A | 6/1973 | Soehngen |
| 3,802,817 A | 4/1974 | Matsuki |
| 3,849,241 A | 11/1974 | Butin et al. |
| 3,909,009 A | 9/1975 | Cvetko et al. |
| 4,044,404 A | 8/1977 | Martin et al. |
| 4,340,563 A | 7/1982 | Appel et al. |
| 4,468,428 A | 8/1984 | Early et al. |
| 4,738,740 A | 4/1988 | Pinchuk et al. |
| 4,965,110 A | 10/1990 | Berry |
| 5,024,789 A | 6/1991 | Berry |
| 5,079,080 A | 1/1992 | Schwarz |
| 5,306,550 A | 4/1994 | Nishiyama et al. |
| 5,464,450 A | 11/1995 | Buscemi et al. |
| 5,591,335 A | 1/1997 | Barboza et al. |
| 5,626,611 A | 5/1997 | Liu et al. |
| 5,634,944 A | 6/1997 | Magram |
| 5,795,584 A | 8/1998 | Totakura et al. |
| 5,851,937 A | 12/1998 | Wu et al. |
| 5,997,568 A | 12/1999 | Liu |
| 6,147,135 A | 11/2000 | Yuan et al. |
| 6,162,535 A | 12/2000 | Turkevich et al. |
| 6,171,338 B1 | 1/2001 | Talja et al. |
| 6,180,848 B1 | 1/2001 | Flament et al. |
| 6,183,670 B1 | 2/2001 | Torobin et al. |
| 6,265,333 B1 | 7/2001 | Dzenis et al. |
| 6,306,424 B1 | 10/2001 | Vyakarnam et al. |
| 6,391,060 B1 | 5/2002 | Ory et al. |
| 6,596,296 B1 | 7/2003 | Nelson et al. |
| 6,630,231 B2 | 10/2003 | Perez et al. |
| 6,649,807 B2 | 11/2003 | Mizutani |
| 6,685,956 B2 | 2/2004 | Chu et al. |
| 6,689,374 B2 | 2/2004 | Chu et al. |
| 6,713,011 B2 | 3/2004 | Chu et al. |
| 6,753,454 B1 | 6/2004 | Smith et al. |
| 6,790,455 B2 | 9/2004 | Chu et al. |
| 6,797,655 B2 | 9/2004 | Rudisill |
| 6,946,506 B2 | 9/2005 | Bond et al. |
| 7,134,857 B2 | 11/2006 | Andrady et al. |
| 7,172,765 B2 | 2/2007 | Chu et al. |
| 7,192,604 B2 | 3/2007 | Brown et al. |
| 7,655,070 B1 | 2/2010 | Dallas et al. |
| 7,759,082 B2 | 7/2010 | Bowlin et al. |
| 7,799,262 B1 | 9/2010 | Kim |
| 7,846,466 B2 | 12/2010 | Shea et al. |
| 7,879,093 B2 | 2/2011 | Wei et al. |
| 7,981,353 B2 | 7/2011 | Mitchell et al. |
| 8,066,932 B2 | 11/2011 | Xu |
| 8,222,166 B2 | 7/2012 | Chu et al. |
| 8,273,369 B2 | 9/2012 | Moloye-Olabisi |
| 8,652,215 B2 | 2/2014 | Bellamkonda et al. |
| 8,728,463 B2 | 5/2014 | Atala et al. |
| 8,728,817 B2 | 5/2014 | Ogle et al. |
| 8,809,212 B1 | 8/2014 | Dirk et al. |
| 8,852,621 B2 | 10/2014 | Patel |
| 9,074,172 B2 | 7/2015 | Johnson |
| 9,085,830 B2 | 7/2015 | Mitchell et al. |
| 9,163,331 B2 | 10/2015 | Atala et al. |
| 9,168,231 B2 | 10/2015 | Patel et al. |
| 9,345,486 B2 | 5/2016 | Zhang et al. |
| 9,393,097 B2 | 7/2016 | McCullen et al. |
| 9,476,026 B2 | 10/2016 | Arinzeh et al. |
| 9,487,893 B2 | 11/2016 | Moore et al. |
| 9,539,365 B2 | 1/2017 | Kasunga et al. |
| 9,572,909 B2 | 2/2017 | Simpson et al. |
| 9,585,666 B2 | 3/2017 | Yu et al. |
| 9,737,632 B2 | 8/2017 | Johnson et al. |
| 9,884,027 B2 | 2/2018 | Johnson |
| 9,938,373 B2 | 4/2018 | Wang et al. |
| 10,016,464 B2 | 7/2018 | Murphy et al. |
| 10,080,687 B2 | 9/2018 | MacEwan |
| 10,124,089 B2 | 11/2018 | MacEwan |
| 10,149,749 B2 | 12/2018 | MacEwan et al. |
| 10,166,315 B2 | 1/2019 | Johnson et al. |
| 10,227,568 B2 | 3/2019 | Johnson |
| 10,231,821 B2 | 3/2019 | Gabriele et al. |
| 10,233,427 B2 | 3/2019 | Johnson |
| 10,239,262 B2 | 3/2019 | Johnson |
| 10,294,449 B2 | 5/2019 | Johnson |
| 10,335,154 B2 | 7/2019 | Johnson et al. |
| 10,363,041 B2 | 7/2019 | Yu et al. |
| 10,381,672 B2 | 8/2019 | Lee et al. |
| 10,405,963 B2 | 9/2019 | McAlpine et al. |
| 10,406,346 B2 | 9/2019 | Scott-Carnell et al. |
| 10,413,574 B2 | 9/2019 | Fong et al. |
| 10,420,856 B2 | 9/2019 | Arinzeh et al. |
| 10,441,403 B1 | 10/2019 | MacEwan et al. |
| 10,441,685 B2 | 10/2019 | MacEwan |
| 10,588,734 B2 | 3/2020 | MacEwan et al. |
| 10,617,512 B2 | 4/2020 | MacEwan |
| 10,632,228 B2 | 4/2020 | MacEwan |
| 10,682,444 B2 | 6/2020 | MacEwan |
| 10,738,152 B2 | 8/2020 | Wang et al. |
| 10,888,409 B2 | 1/2021 | MacEwan |
| 11,000,358 B2 | 5/2021 | MacEwan |
| 11,096,772 B1 | 8/2021 | MacEwan et al. |
| 11,176,234 B2 | 11/2021 | MacEwan et al. |
| 11,224,677 B2 | 1/2022 | MacEwan |
| 11,826,487 B2 | 11/2023 | MacEwan |
| 2002/0081732 A1 | 6/2002 | Bowlin et al. |
| 2002/0090725 A1 | 7/2002 | Simpson et al. |
| 2002/0173213 A1 | 11/2002 | Chu et al. |
| 2002/0192251 A1 | 12/2002 | Collin |
| 2003/0004579 A1 | 1/2003 | Rousseau et al. |
| 2003/0054035 A1 | 3/2003 | Chu et al. |
| 2004/0013819 A1 | 1/2004 | Hou et al. |
| 2004/0018226 A1 | 1/2004 | Wnek et al. |
| 2004/0037813 A1 | 2/2004 | Simpson et al. |
| 2004/0096532 A1 | 5/2004 | Dubson et al. |
| 2004/0102614 A1 | 5/2004 | Islam et al. |
| 2005/0104258 A1 | 5/2005 | Lennhoff |
| 2005/0167311 A1 | 8/2005 | Tonsfeldt et al. |
| 2005/0222591 A1 | 10/2005 | Gingras et al. |
| 2006/0014460 A1 | 1/2006 | Alexander Isele et al. |
| 2006/0085063 A1 | 4/2006 | Shastri et al. |
| 2006/0094320 A1 | 5/2006 | Chen et al. |
| 2006/0153904 A1 | 7/2006 | Smith et al. |
| 2006/0193578 A1 | 8/2006 | Ouderkirk et al. |
| 2006/0204539 A1 | 9/2006 | Atala et al. |
| 2006/0240110 A1 | 10/2006 | Kiick et al. |
| 2006/0246798 A1 | 11/2006 | Reneker et al. |
| 2006/0263417 A1 | 11/2006 | Lelkes et al. |
| 2006/0264140 A1 | 11/2006 | Andrady |
| 2007/0073344 A1 | 3/2007 | Jahns et al. |
| 2007/0152378 A1 | 7/2007 | Kim |
| 2007/0155273 A1 | 7/2007 | Chu et al. |
| 2007/0225631 A1 | 9/2007 | Bowlin et al. |
| 2007/0269481 A1 | 11/2007 | Li et al. |
| 2008/0065123 A1 | 3/2008 | Yli-Urpo et al. |
| 2008/0112998 A1 | 5/2008 | Wang |
| 2008/0207798 A1 | 8/2008 | Hellring et al. |
| 2008/0208358 A1 | 8/2008 | Bellamkoda et al. |
| 2008/0220042 A1 | 9/2008 | Hashi et al. |
| 2008/0237934 A1 | 10/2008 | Reneker et al. |
| 2009/0028921 A1 | 1/2009 | Arinzeh |
| 2009/0074832 A1 | 3/2009 | Zussman et al. |
| 2009/0075354 A1 | 3/2009 | Reneker et al. |
| 2009/0155326 A1 | 6/2009 | Mack et al. |
| 2009/0162468 A1 | 6/2009 | Barinov et al. |
| 2009/0171467 A1 | 7/2009 | Mann et al. |
| 2009/0202616 A1 | 8/2009 | Chong et al. |
| 2009/0214614 A1 | 8/2009 | Everland et al. |
| 2009/0228021 A1 | 9/2009 | Leung |
| 2009/0317446 A1 | 12/2009 | Tan et al. |
| 2010/0003305 A1 | 1/2010 | Pattanaik |

(56) References Cited

U.S. PATENT DOCUMENTS

| | | |
|---|---|---|
| 2010/0047309 A1 | 2/2010 | Lu et al. |
| 2010/0061962 A1 | 3/2010 | Li |
| 2010/0076377 A1 | 3/2010 | Ehrenreich et al. |
| 2010/0092687 A1 | 4/2010 | Sumida et al. |
| 2010/0093093 A1 | 4/2010 | Leong et al. |
| 2010/0119564 A1 | 5/2010 | Kasuga et al. |
| 2010/0120115 A1 | 5/2010 | Ogle et al. |
| 2010/0137902 A1 | 6/2010 | Lee et al. |
| 2010/0166854 A1 | 7/2010 | Michniak-Kohn et al. |
| 2010/0174368 A1 | 7/2010 | Lynch et al. |
| 2010/0179659 A1 | 7/2010 | Li et al. |
| 2010/0185219 A1 | 7/2010 | Gertzman et al. |
| 2010/0190254 A1 | 7/2010 | Chian et al. |
| 2010/0233115 A1* | 9/2010 | Patel .................. A61L 15/26 425/174.8 E |
| 2010/0273258 A1 | 10/2010 | Lannutti et al. |
| 2010/0291182 A1 | 11/2010 | Palasis et al. |
| 2010/0292791 A1 | 11/2010 | Lu et al. |
| 2010/0297208 A1 | 11/2010 | Fry et al. |
| 2010/0330419 A1 | 12/2010 | Cui et al. |
| 2010/0331980 A1 | 12/2010 | Lee et al. |
| 2011/0014289 A1 | 1/2011 | Datta et al. |
| 2011/0087277 A1 | 4/2011 | Viola et al. |
| 2011/0098826 A1 | 4/2011 | Mauck et al. |
| 2011/0101571 A1 | 5/2011 | Reneker |
| 2011/0111012 A1 | 5/2011 | Pepper et al. |
| 2011/0150973 A1 | 6/2011 | Bowlin et al. |
| 2011/0152897 A1 | 6/2011 | Bates |
| 2011/0174158 A1 | 7/2011 | Walls et al. |
| 2011/0180951 A1 | 7/2011 | Teo et al. |
| 2011/0242310 A1 | 10/2011 | Beebe, Jr. et al. |
| 2011/0280919 A1 | 11/2011 | Moloye-Olabisi et al. |
| 2011/0287082 A1 | 11/2011 | Smith et al. |
| 2012/0015331 A1 | 1/2012 | Wood et al. |
| 2012/0029654 A1 | 2/2012 | Xu et al. |
| 2012/0040581 A1 | 2/2012 | Kim |
| 2012/0123342 A1 | 5/2012 | Andrews et al. |
| 2012/0165957 A1 | 6/2012 | Everland et al. |
| 2012/0221025 A1 | 8/2012 | Simpson et al. |
| 2012/0225039 A1 | 9/2012 | Li et al. |
| 2012/0265300 A1 | 10/2012 | Mauck et al. |
| 2012/0310260 A1 | 12/2012 | Hamlin et al. |
| 2012/0330437 A1 | 12/2012 | El-Kurdi et al. |
| 2013/0030548 A1 | 1/2013 | Ling |
| 2013/0035704 A1 | 2/2013 | Dudai |
| 2013/0110138 A1 | 2/2013 | Hurtado et al. |
| 2013/0115457 A1 | 5/2013 | Haynie et al. |
| 2013/0144249 A1 | 6/2013 | Fenton et al. |
| 2013/0197663 A1 | 8/2013 | MacEwan et al. |
| 2013/0251762 A1 | 9/2013 | Wei et al. |
| 2013/0338791 A1 | 12/2013 | McCullen et al. |
| 2014/0030315 A1 | 1/2014 | Johnson |
| 2014/0081297 A1 | 3/2014 | Hoke et al. |
| 2014/0128345 A1 | 5/2014 | Woodrow et al. |
| 2014/0272225 A1 | 9/2014 | Johnson |
| 2014/0288663 A1 | 9/2014 | Borden et al. |
| 2014/0303727 A1 | 10/2014 | Atlas et al. |
| 2014/0322512 A1 | 10/2014 | Pham et al. |
| 2015/0045818 A1 | 2/2015 | Kim et al. |
| 2015/0132423 A1 | 5/2015 | Johnson |
| 2015/0133454 A1 | 5/2015 | Choy et al. |
| 2015/0190285 A1 | 7/2015 | MacEwan |
| 2015/0250927 A1 | 9/2015 | MacEwan |
| 2015/0297791 A1 | 10/2015 | Patel et al. |
| 2015/0342719 A1 | 12/2015 | Chen et al. |
| 2016/0022873 A1 | 1/2016 | Besner et al. |
| 2016/0083692 A1 | 3/2016 | Hardy et al. |
| 2016/0083868 A1 | 3/2016 | Park |
| 2016/0136330 A1 | 5/2016 | Benkirane-Jessel et al. |
| 2016/0302869 A1 | 10/2016 | Chopra |
| 2016/0317706 A1 | 11/2016 | Johnson |
| 2017/0095591 A1 | 4/2017 | Zuhaib et al. |
| 2017/0119886 A1 | 5/2017 | Johnson et al. |
| 2017/0182206 A1 | 6/2017 | Johnson et al. |
| 2017/0182211 A1 | 6/2017 | Raxworthy et al. |
| 2017/0319323 A1 | 11/2017 | MacEwan |
| 2017/0319742 A1 | 11/2017 | Johnson et al. |
| 2018/0116973 A1 | 5/2018 | Johnson |
| 2018/0161185 A1 | 6/2018 | Kresslein et al. |
| 2018/0174367 A1 | 6/2018 | Marom et al. |
| 2018/0221537 A1 | 8/2018 | Johnson et al. |
| 2018/0237952 A1 | 8/2018 | Johnson et al. |
| 2018/0245243 A1 | 8/2018 | Krieger et al. |
| 2018/0263919 A1 | 9/2018 | Hoke et al. |
| 2018/0368917 A1 | 12/2018 | Dekel et al. |
| 2019/0015563 A1 | 1/2019 | MacEwan |
| 2019/0021837 A1 | 1/2019 | MacEwan et al. |
| 2019/0054036 A1 | 2/2019 | Johnson et al. |
| 2019/0102880 A1 | 4/2019 | Parpara et al. |
| 2019/0105128 A1 | 4/2019 | Velazquez et al. |
| 2019/0134267 A1 | 5/2019 | Francis et al. |
| 2019/0134570 A1 | 5/2019 | Pintauro et al. |
| 2019/0153398 A1 | 5/2019 | Johnson |
| 2019/0249127 A1 | 5/2019 | Johnson |
| 2019/0175786 A1 | 6/2019 | Cohen et al. |
| 2019/0269829 A1 | 9/2019 | Johnson et al. |
| 2019/0271098 A1 | 9/2019 | Johnson et al. |
| 2019/0282351 A1 | 9/2019 | Mathisen et al. |
| 2019/0328393 A1 | 10/2019 | Yu et al. |
| 2019/0330419 A1 | 10/2019 | Song et al. |
| 2019/0350688 A1 | 11/2019 | Hurtado et al. |
| 2019/0365520 A1 | 12/2019 | MacEwan |
| 2019/0365958 A1 | 12/2019 | MacEwan |
| 2019/0374227 A1 | 12/2019 | Johnson et al. |
| 2020/0000570 A1 | 1/2020 | MacEwan et al. |
| 2020/0046883 A1 | 2/2020 | Martin et al. |
| 2020/0060800 A1 | 2/2020 | MacEwan et al. |
| 2020/0197153 A1 | 6/2020 | MacEwan et al. |
| 2020/0229679 A1 | 7/2020 | Zhao et al. |
| 2020/0242767 A1 | 7/2020 | Zhao et al. |
| 2020/0277711 A1 | 9/2020 | Xie |
| 2021/0001014 A1 | 1/2021 | MacEwan |
| 2021/0030525 A1 | 2/2021 | MacEwan et al. |
| 2021/0052362 A1 | 2/2021 | MacEwan et al. |
| 2021/0128792 A1 | 5/2021 | Dunbar et al. |
| 2021/0228782 A1 | 7/2021 | MacEwan |
| 2021/0267746 A1 | 9/2021 | MacEwan et al. |
| 2021/0338408 A1 | 11/2021 | MacEwan et al. |
| 2023/0030107 A1 | 2/2023 | MacEwan et al. |
| 2023/0033599 A1 | 2/2023 | MacEwan et al. |

FOREIGN PATENT DOCUMENTS

| | | |
|---|---|---|
| CA | 2094908 C | 2/2000 |
| CA | 2386810 C | 9/2013 |
| CA | 2802482 | 6/2017 |
| CN | 102260963 | 11/2011 |
| CN | 102691176 | 9/2012 |
| CN | 103599562 | 2/2014 |
| CN | 104894750 | 9/2015 |
| DE | 102014107826 A1 | 12/2014 |
| EP | 0314109 | 5/1989 |
| EP | 0515522 B1 | 10/1993 |
| EP | 0571415 | 7/1995 |
| EP | 0757127 | 2/1997 |
| EP | 2045375 | 3/2011 |
| EP | 2358301 | 8/2011 |
| EP | 2599858 | 6/2013 |
| EP | 2582823 | 3/2018 |
| EP | 2897561 | 4/2020 |
| EP | 3508641 | 8/2020 |
| EP | 3741896 | 11/2020 |
| GB | 1286858 | 8/1972 |
| GB | 2181207 | 4/1987 |
| GB | 2195251 | 4/1988 |
| JP | H03161563 | 7/1991 |
| JP | 3487722 B2 | 1/2004 |
| JP | 2005-534828 | 11/2005 |
| JP | 2006-283241 | 10/2006 |
| JP | 2006-328562 | 12/2006 |
| JP | 2007-303021 | 11/2007 |
| JP | 2008-223186 | 9/2008 |
| JP | 2009061109 | 3/2009 |
| JP | 2011-059786 | 3/2011 |

(56) References Cited

FOREIGN PATENT DOCUMENTS

| | | |
|---|---|---|
| JP | 2011-509786 | 3/2011 |
| JP | 4769871 | 9/2011 |
| JP | 4979264 | 7/2012 |
| JP | 2012-528464 | 11/2012 |
| JP | 2013-518996 | 5/2013 |
| JP | 2013-534979 | 9/2013 |
| JP | 6295258 | 3/2018 |
| JP | 6328672 | 5/2018 |
| KR | 100439871 B1 | 7/2004 |
| KR | 2006-0118937 | 11/2006 |
| KR | 10-2007-0047873 | 5/2007 |
| KR | 10-1703095 | 2/2017 |
| SG | 186379 | 1/2013 |
| SG | 11201502207 W | 4/2015 |
| WO | WO 1991/001695 | 2/1991 |
| WO | WO 01/27365 | 4/2001 |
| WO | WO 02/00149 | 1/2002 |
| WO | WO 2004/016839 | 2/2004 |
| WO | WO 2006/096791 | 9/2006 |
| WO | WO 2006/123858 | 11/2006 |
| WO | WO 2007/086910 | 8/2007 |
| WO | WO 2008/069760 | 6/2008 |
| WO | WO 2009/093023 | 7/2009 |
| WO | WO 2010/041944 | 4/2010 |
| WO | WO 2010/042651 | 4/2010 |
| WO | WO 2010/112564 | 10/2010 |
| WO | WO 2010/138619 | 12/2010 |
| WO | WO 2011/095141 | 8/2011 |
| WO | WO 2011/159889 | 12/2011 |
| WO | WO 2012/080706 | 6/2012 |
| WO | WO 2013/106822 | 1/2013 |
| WO | WO 2013/025819 | 2/2013 |
| WO | WO 2013/050428 | 4/2013 |
| WO | WO 2013/078051 | 5/2013 |
| WO | WO 2014/031721 | 2/2014 |
| WO | WO 2014046669 | 3/2014 |
| WO | WO 2014/145864 | 9/2014 |
| WO | WO 2014/152906 | 9/2014 |
| WO | WO 2015/048224 | 4/2015 |
| WO | WO 2015/116917 | 8/2015 |
| WO | WO 2015/153011 | 10/2015 |
| WO | WO 2015/157485 | 10/2015 |
| WO | WO 2016/176559 | 11/2016 |
| WO | WO 2017/024263 | 2/2017 |
| WO | WO 2017/035500 | 3/2017 |
| WO | WO 2017/044982 | 3/2017 |
| WO | WO 2017/079328 | 5/2017 |
| WO | WO 2017/196325 | 11/2017 |
| WO | WO 2018/112203 | 6/2018 |
| WO | WO 2018/144858 | 8/2018 |
| WO | WO 2023/007443 | 2/2023 |
| WO | WO 2023/007444 | 2/2023 |

OTHER PUBLICATIONS

Xing et al, Multi Material ElectroSpinniing From Methods to Biomedical Applications, Mater. Toda Bio. (Year: 2023).*
Kim et al (A Controlled Design of Aligned and Random Nanofibers for 3D Bi-functionalized Nerve Conduits Fabricated via a Novel Electrospinning Set-Up, Scientific Reports (6238761) . (Year: 2016).*
Xie et al, Nerve Guidance Conduits Based on Double-Layered Scaffolds of Electrospun Nanofibers for Repairing the Peripheral Nervous System, ACS Appl Mater Interface; 6(12): 9472-9480. (Year: 2014).*
Panseri et al., "Electrospun micro- and nanofiber tubes for functional nervous regeneration in sciatic nerve transections." BMC Biotechnol. Apr. 11, 2008;8:39.
Kim, et al., Controlled Design of Aligned and Random Nanofibers for 3D Bi-functionalized Nerve Conduits Fabricated via a Novel Electrospinning Set-up. Sci Rep 6, 23761 (2016).
Quan et al., "Aligned fibers enhance nerve guide conduits when bridging peripheral nerve defects focused on early repair stage." Neural Regeneration Research 14(5):p. 903-912, May 2019.
Gnavi et al., "The influence of electrospun fibre size on Schwann cell behaviour and axonal outgrowth." Mater Sci Eng C Mater Biol Appl. Mar. 2015;48:620-31.
International Search Report dated Feb. 3, 2023 in PCT/US22/75995 Filed Sep. 6, 2022.
U.S. Appl. No. 62/154,286, filed Apr. 29, 2015, Johnson.
3rd International Conference on Electrospinning Conference Program dated Aug. 4-7, 2004, www.ceramics.org/electrospin2014.
ASTM International, "Standard Guide for Assessing Microstructure of Polymeric Scaffolds for Use in Tissue-Engineered Medical Products" dated Mar. 27, 2013.
Barbol T et al. Biocompability evaluation of dura maTer substitutes in an animal model. Neurological research2001; vol. 23 pp. 813-820.
Beachley V et al. "Polymer nanofibrous structures: Fabrication, biofunctionalization, and cell interactions." Prog Polym Sci. 2010;35(7) pp. 868-892.
Beheshtkhoo et al. "Fabrication and Properties of Collagen and Polyurethane Polymeric Nanofibers Using Electrospinning Techniques" Journal of Environmental Treatment Techniques 2019, vol. 7, Issue 4, pp. 802-807.
Bhattaral et al. "Electrospun chitosa-based nanofibers and their cellular compatibility", Biomaterials, vol. 26, Issue 31, Nov. 2005, pp. 6176-6184.
Bognitzki et al., "Nanostructured Fibers via Electrospinning", Advanced Mater. 2001, 13. No. 1, Jan. 5, pp. 70-72.
Bognitzki et al., "Preparation of Fibers with Nanoscaled Morphologies: Electrospinning of Polmer Blends" Polymer Enginering and Science, Jun. 2001, vol. 41, No. 6, pp. 982-989.
Boland et al., "Tailoring Tissue Engineering Scaffords Using Elactrostatic Proceedings Techniques: A Study of Poly(Glycolic acid) Electrospinning," Journal of Macromolecular Science 38:1231-1243 (2001), doi: 10.1081/MA-100108380.
Camposeo et al., "Lobal Mechanical Properties of Electrospun Fibers Correlate to Their Internal Nanostructure" Nano Lett. 2013, pp. 13, 5056-5062.
Chen et al. "Electrospun 3D Fibrous Scaffolds for Chronic Wound Repair," 2016, Materials 9(272):1-12.
Chen, Rul, et al. "Preparation and characterization of coaxial electrospun thermoplastic polyurethane/collagen compound nanofibers for tissue engineering applications." Colloids and Surfaces B: Biointerfaces 79.2 (2010) pp. 315-325.
Chen, Rul, et al. "Preparation and Study of TPU/Collagen Complex Nanofiber via Electrospinning." AATCC review 10.2 (2010).
Cheng et al., "Engineering the Microstructure of Electrospun Fibrous Scaffolds by Microtopography," Biomacromolecules 14:1349-1360 (2013), doi: 10.1021/bm302000n).
Choi, Sung-Seen, et al. "Formation of interfiber bonding in electrospun poly (etherimide) nanofiber web." Journal of materials science 39.4 (2004) pp. 1511-1513.
Chong et al., "Evaluation of electrospun PCL/gelatin nanofibrous scaffold for wound healing and layered dermal reconstruction," Acta Biomaterialla 3:321-330 (2007) doi: 10.1016/j.actbio.2007.10.002 (2007).
Clark et al. "Investigation of the Effects of Cell Seeding on Neotissue Formation in a Tissue Engineered Trachea" J Pediatr Surg. Jan. 2016; 51(1) 49-55.
Cole et al. A comparative long-term assessment of four soft tissue substitutes. Aesthetic surgery journal I theAmerican Society for Aesthetic Plastic surgery 2011; vol. 31 pp. 674-681.
Cui et al., "Controlled assembly of poly(vinyl pyrrolidone) fibers through an electric-field-assisted electrospinning method," Applied Physics A, 103(1): 167-172 (2011).
Davis, et al., "A biodegradable compsite artifical tendon," Journal of Materials Science: Materials in Medicine 3,359-364 (1992).
Deitzel et al. "The effect of processing variables on the morphology of electrospun nanofibers and textiles" Polymer 42 (2001) pp. 261-272.
Dempsey et al., "Micropatterning of Electrospun Polyurethane Fibers Through Control of Surface Topography," Macromolecular Materials and Engineering 295: 990-994 (2020), doi: 10.1002/mame. 201000152.

(56) References Cited

OTHER PUBLICATIONS

Dhandayuthapani et al. "Polymeric Scaffolds in Tissue Engineering Application: A Review" 2011, International Journal of Polymer Science 2011, Article ID 290602, 19 pages.
Diaz et al., "Fabrication of structured micro and nanofibers by coaxial electrospinning," Journal of Physics, Conference Series 127: 1-8 (2008), goi: 10.1088/1742-6596/127/1/012008.
Ding et al., "Fabrication of blend biodegradeable nanofibrous nonwoven mats via multi-jet electrospinning," Polymer 45: 1895-1902 (2004), doi: 10.1016/j.polymer.2004.01.026.
Doshi, et al., "Electrospinning Process and Applications of Electrospun Fibers" 35 J. Electrostatics 151 (1995).
Dubsky et al., "Nanofibers prepared by needleless electrospinning technology as scaffolds for wound healing," J Mater Sci: Mater Med, DOI 10.1007/s 10856-012-4577-7, Feb. 2012.
Dzenis et al., "Hierarchical nano-/micromaterials based on electrospun polymer fibers: Predictive models for thermomechanical behavior" Journal of Computer-Aided Materials Design, pp. 3, 403-408 (1996).
Dzenis et al., "Polymer Hybrid Nano/Micro Composites," Proceedings of the American Society for Composites Ninth Technical Conference, pp. 657-665, 1994.
Fang et al. "Electrospinning: an advanced nanofiber production technology." In: H. Niu, H. Zhou and H. Wang (Eds.), Energy Harvesting Properties of Electrospun Nanofibers (1st ed. [online], pp. 1-Jan. 1, 44). IOP Publishing Ltd. (2020). https://lopscience.lop.org/book/978-0-7503-2005-4/chapter/bk978-0-7503-2005-4ch1 (Accessed Apr. 6, 2021), dol 10.1088/978-0-7503-2005-4ch1.
Figallo et al. "Micropatterned biopolymer 3D scaffold for static and dynamic culture of human fibroblasts" Biotechnol Prog. Jan-Feb. 2007;23(1):210-6. doi: 10.1021/bp0602092.
Foy, et al., Allergic reaction to a bovine dural substitute following spinal cord untethering. Case report, Journal of Neurosurgery Pediatrics 2008; vol. 1, pp. 167-169.
Fridrikh, et al., "Controlling the Fiber Diameter during Electrospinning" The American Physical Society 2003; vol. 90, No. 14.
Gibson, et al., Electrospun Fiber Mais: Transport Properties, AIChE Journal, 1999, vol. 45, No. 1, pp. 190-195.
Grafe et al., "Nanofiber Webs from Electrospinning," Nonwovens in Filtration —Fifth International Conference (2003).
Huang et al., "A review on polymer nanofibers by electrospinning and their applications in nanocomposites," Composites Science and Technology 63: 2223-2253 (2003), doi: 10.1016/S0266-3538(03)00178-7.
Huang, et al., "Generation of Synthetic Elastin-Mimetic Small Diameter Fibers and Fiber Networks", Macromolecules 2000, 33, 2989-2997.
Jaeger, et al. "Electrospinning of Ultra-Thin Polymer Fibers", Macromol. Symp. 127, 141-150 (1998).
Ju et al., "Bilayered scaffold for engineering cellularized blood vessels, " Biomaterials 31: 4313-4321 (2010), doi: 10.1016/j.biomaterials.2010.02.002.
Kenawy et al., "Release of tetracycline hydrochloride from electrospun poly(ethylene-co-vinylacetate), poly(lactic acid), and a blend," Journal of Controlled Release 81: 57-64 (2002), doi: 10.1016/S0168-3659(02)00041-X.
Khil et al., "Novel Fabricated Matrix Via Electrospinning for Tissue Engineering," Wiley Periodicals, Inc. 2004.
Kidoaki et al., "Mesoscopic spatial designs of nano- and microfiber meshes for tissue-engineering matrix and scaffold based on newly devised multilayering and mixing electrospinning techniques," Biomaterials 26: 37-46 (2005), doi: 10.1016/j.biomaterials.2004.01.063.
Kumar et al., "Nanofibers: Effective Generation by Electrospinning and Their Applications," Journal of Nanoscience and Nanotechnology, vol. 12, 1-25, 2012.
Le et al., "Engineering a Biocompatible Scaffold with Either Micrometre or Nanometre Scale Surface Topography for Promoting Protein Adsorption and Cellular Response," International Journal of Biomaterials 2013: 1-16 (2013), doi: 10.115/2013/782549.

Lee et al., "Development of a composite vascular scaffolding system that withstands physiological vascular conditions," Biomaterials 29: 2891-2898 (2008), doi: 10.1016/j.biomaterials.2008.03.032.
Li et al., "Direct Fabrication of Composite and Ceramic Hollow Nanofibers by Electrospinning" Nano Lett. 2004, 4, 933-938.
Li et al., "Electrospinning of Nanofibers: Reinventing the Wheel?" Adv. Mater. 11.2004, 16, 1151-1170.
Li, et al., "Electrospinning Nanofibers as Uniaxially Aligned Arrays and Layer-by-Layer Stacked Films" Adv. Mater. 2004, 16, 361-36.
Li, et al., "Electrospinning of Polymeric and Ceramic Nanofibers as 20 Unlaxially Aligned Arrays" Nano Lett. 2003, 3, 1167-1171.
Liu et al., "Electrospun Fibrous Mats on Lithographically Micropatterned Collectors to Control Cellular Behaviors," Langmuir 28:17134-17142 (2012), doi: 10.1021/la303490x).
Liu, L-Q et al. "Tensile mechanics of electrospun multiwalled nanotube/poly (methyl methacrylate) nanofibers." Advanced Materials 19.9 (2007) pp. 1228-1233.
Macewan et al., "What makes the optimal wound healing material? A review of current science and introduction of a synthetic nanofabricated wound care scaffold", Cureus, vol. 9(10):1-12 (2017).
Madhugiri, S et al., "Electrospun MEH-PPV/SBA-15 Composite Nanofibers Using a Dual Syringe Method," J. Am. Chem. Soc., 125: 14531-14538 (2003).
Manavitehrani et al. "Biomedical Applications of Biodegradable Polyesters" 2016, Polymers 8(20):1-32.
Martinez-Lage et al., "Accidental transmission of Creutzfeldt-Jakob disease by dural cadaveric grafts," Journal of Neurology, Neurosurgery & Psychiatry, 57(9): 1091-1094 (1994).
McClure et al., "The use of air-flow impedance to control fiber deposition patterns during electrospinning," Biomaterials 33: 771-779 (2012), doi: 10.1016/j.biomaterials.2011.10.011.
McMillan et al. "Small diameter porous poly (&-caprolactone) films enhance adhesion and growth of human cultured epidermal keratinocyte and dermal fibroblast cells", Tissue Eng. (2007) Apr. 13(4): pp. 789-798.
Mi et al. "Asymmetric chitosan membranes prepared by dry/west phase separation: a new type of wound dressing for controlled antibacterial release", Journal of Membrane Science, (vol. 212) pp. 237-254.
Murthy et al. "Biodegradation of Polymers" 2012, Polymer Science: A Comprehensive Reference, 9:547-560.
Norris et al. "Electrostatic fabrication of ultrafine conducting fibers: polyaniline/polyethylene oxide blends" Synthetic Metals 114 (2000) pp. 109-114.
Park, S. et al., Apparatus for Preparing Electrospun Nanofibers: Designing and Electrospinning process for Nanofiber Fabrication, Polymer International, 2007, pp. 1361-1366.
Pepper et al., "Factors Influencing Poor Outcomes in Synthetic Tissue-Engineered Tracheal Replacement" Otolaryngol Head Neck Surg. Sep. 2019; 161(3): 458-467.
Pham et al. "Electrospun poly (E-caprolactone) microfiber and multilayer nanofiber/microfiber scaffold: characterization of scaffolds and measurement of cellular infiltration", Biomacromolecules 2006, pp. 7, 10, 2796-2805, Pub. Sep. 23, 2006.
Pham et al., "Electrospinning of Polymeric Nanofibers for Tissue Engineering Applications: A Review", Tissue Engineering, 12(5): 1197-1211 (2006).
Ramakrishna et al., "Electrospun nanofibers: solving global issues," Materials Today 9: 40-50 (2006), doi: 10.1016/S1369-7021(06)71389-X.
Rieger et al. "Designing electrospun nanofiber mats to promote wound healing—a review," J. Mater. Chem. B, 2013, 1, 4531.
Schneider et al. "Influence of pH on Wound-healing: a New Perspective for Wound-therapy" 2007 Arch. Dermatol. Res. 298:413-420.
Shin, et al. "Experimental characterization of electrospinning: the electrically forced jet and instabilities" Polymer 42 (2001) 9955-9967.
Shin, Ho Joon, et al. "Electrospun PLGA nanofiber scaffolds for articular cartilage reconstruction: mechanical stability, degradation and cellular responses under mechanical simulation in vitro." Journal of Biomaterials Science, Polymer Edition 17.1-2 (2006) pp. 103-119.

(56) References Cited

OTHER PUBLICATIONS

Smith et al., "Suture-reinforced electrospun polydioxanone-elastin small-diameter tubes for use in vascular tissue engineering: a feasibility study," Acta Biomaterialia 4: 58-66 (2008), doi: 10.1016/j.actbio.2007.08.001.
Stitzel et al., "Arterial Smooth Muscle Cell Proliferation on a Novel Biomimicking, Biodegradeable Vascular Graft Scaffold," Journal of Biomaterials Applications 16: 22-33 (2001), doi: 10.1106/U2UU-M9QH-YOBB-5GYL.
Subbiah et al. "Electrospinning of Nanofibers," J. of Applied Polymer Science, 96: 55-569 (2005).
Tan et al., "Tensile test of a single nanofiber using an atomic force microscope tip", Applied Physics Letters 86, 073115 (2005).
Teo W et al. "Electrospun scaffold tailored for tussie-specific extracellular matrix." Biotechnol J Healthc Nutr Technol. 2006;1(9):918-29.
Thomas et al. "Electrospun bioactive nanocomposite scaffolds of polycaprolactone and nanohydroxyapatite for bone tissue engineering", J Nanosci Nanotechnol. Feb. 2006;6(2):487-93. doi: 10.1166/jnn.2006.097.
Tormala, et al., "Ultra-High-Strength absorable self-reinforeced polyglycolide (SR-PGA) composite rods for internal fixation of bone fractures: In vitro and in vivo study" Journal of Biomedical Materials Research, Jan. 1991.
Valizadeh et al., "Electrospinning and electrospun nanofibres," IET Nanobiotechnol., 2014, vol. 8, Iss. 2, pp. 83-92.
Vaz et al. "Design of scaffold for blood vessel tissue engineering using a multiple-layering electrospinning technique" Acta Biomater/ Sep. 2005;1(5):572-82. doi:10.1016/j.actbio.2005.06.006. Epub Jul. 26, 2005. https://pubmed.ncbi.nlm.nih.gov/16701837/.
Wikipedia, "Polyhydroxyethylmethacrylate," downloaded on Dec. 18, 2019 from.
Wise Histologic proof that acellular dermal matrices (ADM)—Enduragen DermaMalrix and DuraMatrix—are not repopulaled or nonviable and that AlloDerm may be repopulated but degraded synchronously. Aesthetic surgery Journal / the American Society for Aesthetic Plastic surgery 2012; vol. 32 pp. 355-358.
Wulkersdorfer, "Bimodal Porous Scaffolds by Sequential Electrospinning of Poly(glycolic acid) with Sucrose Particles," International Journal of Polymer Science 2010: 1-9 (2010), doi: 10.1155/2010/436178.
Xie et al., Putting electrospun nanofibers to work for biomedical research. Macromol Rapid Commun 2008; 29, 1775-1792.
Xie, et al., Conductive core-sheath nanofibers and their potential applications in neural tissue engineering. Adv Funct Mater 2009; 19, 2312-2318.
Xie, et al., Neurites outgrowth on nanofiber scaffolds with different orders, structures, and surface properties. ACS Nano 2009; 3, 1151-1159.
Xie, et al., Radially Aligned, Electrospun Nanofibers as Dural Substitutes for Wound Closure and Tissue Regeneration Applicalion, ACS Nano, 2010, vol. 4, No. 9, pp. 5027-5036.
Yarin, et al., "Taylor Cone and Jetting from Liquid Driplets in Electrospinning of Nanofibers," (2001). College of Polymer Science and Polymer Engineering. 85.
Yogeshwar et al., "Electrospinning of Type I Collagen and PCL Nanofibers Using Acetic Acid," Wiley Online Library, Feb. 1, 2012.
Zerris, et al., Repair of the dura mater with processed collagen devices. Journal of biomedical materials research Part B, Applied biomaterials 2007; vol. 83, pp. 580-588.
Zong, Xinhua, et al. "Structure and process relationship of electrospun bloabsorbable nanofiber membranes." Polymer 43.16 (2002) pp. 4403-4412.
Australian Examination Report issued for Application No. 2011268321, dated Apr. 17, 2015 (4 pages).
Australian Examination Report No. 1 issued for Application No. 2016406314 dated Oct. 29, 2020 (4 pages).
Australian Examination Report No. 1 issued for Application No. 2012390291 dated May 31, 2017 (4 pages).
Australian Examination Report No. 1 issued for Application No. 2017232208 dated Jan. 8, 2018 (4 pages).
Australian Examination Report No. 2 issued for Application No. 2016406314 dated 12, Mar. 2021.
Australian Examination Report No. 3 issued for Application No. 2016406314 dated Jul. 5, 2021.
Brazil Technical Report for related Application No. BR112012032169-2, dated Feb. 20, 2019, 4 pages.
Brazil Technical Report for related Application No. BR112015006301-2, dated Oct. 15, 2020, 5 pages.
Canadian Examiner's Report issued for Application No. 2,885,682, dated Jun. 4, 2018 (5 pages).
China Examiner's Report issued for Application No. 201680087078.9, dated Jan. 20, 2021 with translation in 28 pages.
China Second Office Action for Application No. 201680087078.9 dated Jul. 14, 2021 with translation in 28 pages.
European Examination Report issued for Application No. 12884789.4 dated Feb. 13, 2018 (5 pages).
European Extended Search Report in Application No. 16901840.5 dated Dec. 2, 2019 in 10 pages.
European Extended Search Report issued for Application No. 11796426.2, dated Mar. 27, 2014 (6 pages).
European Extended Search Report issued for Application No. 12884789, on Jun. 16, 2016 (12 pages).
European Office Action for application No. 16901840.5, dated Sep. 10, 2021.
European Search Report and Written Opinion for EP application No. 18164340, dated May 17, 2019, 5 pages.
European Search Report and Written Opinion for EP application No. 20175280.5, dated Sep. 11, 2020 in 8 pages.
European Supplementary Partial Search Report issued for Application No. 12884789, dated Feb. 29, 2016 (8 pages).
GCC Examination Report in Application No. GC 2017-33397 dated Apr. 15, 2019 in 4 pages.
Indian Examination Report issued for Application No. 11141/DELNP/2012, dated Jun. 21, 2018 (7 pages).
Indian First Examination Report for IN Application No. 2299/DELNP/2015, dated Oct. 24, 2019, 6 pages.
Indian Frist Examination Report for IN Application No. 201817046790, dated Sep. 29, 2021, 6 pages.
Japanese Office action issued for Application No. 2013-515511, dated Oct. 28, 2014.
Japanese Office Action Summary issued for Application No. 2015-533026, dated Oct. 18, 2016 (5 pages).
Japanese Office translation issued for Application No. 2015-533026, dated Jun. 27, 2017 (4 pages).
PCT International Preliminary Report on Patentability for PCT/US2011/040691, issued Dec. 19, 2012, 9 pages.
PCT International Search Report and Written Opinion issued for Application No. PCT/2011/040691, dated Feb. 24, 2012.
PCT International Search Report and Written Opinion of International Application No. PCT/US2012/056548 dated Apr. 26, 2013 in 14 pages.
PCT International Search Report in International Application No. PCT/US16/32001 dated Aug. 11, 2016 in 1 page.
Singapore Examination Report issued for Application No. 11201502207W, dated Jun. 13, 2017 (8 pages).
Singapore Search and Examination Report for SG 2012092888, issued May 15, 2014, 17 pgs.
Singapore Search and Examination Report for SG 2012092888, issued Jan. 30, 2015, 8 pgs.
International Search Report and Written Opinion in application no. PCT/IB2022/057029, mailed on Oct. 18, 2022, in 8 pages.
International Search Report and Written Opinion in application no. PCT/IB2022/057028, mailed on Jan. 6, 2023, in 9 pages.
Declaration of Gary E. Wnek, PH.D. in support of Petition for Inter Partes Review of U.S. Pat. No. 10632228.
Defendants' Initial Invalidity Contentions in Civil Action No. 20-980-CFC-JLH dated Nov. 4, 2021 in 618 pages.
Petition for Inter Partes Review of U.S. Pat. No. 10,632,228 dated May 28, 2021 in 91 pages.
Report and Recommendation filed May 25, 2023, in Case No. 1:20-cv-00980-CFC-JLH, Document 201, *Acera Surgical, Inc.*,

(56) References Cited

OTHER PUBLICATIONS

*Retectix, LLC, and Washington University*, Plaintiffs, v. *Nanofiber Solutions, LLC, Paragen Technologies LLC, Atreon Orthopedics LLC, and Renovoderm LLC*, Defendants, and *Nanofiber Solutions, LLC, and The Research Foundation for the State University of New York*, Counterclaim Plaintiffs, v. *Acera Surgical, Inc.*, Counterclaim Defendant, in 11 pages.

Joint Appendix to Claim Construction Brief filed Mar. 31, 2023, in Case No. 1:20-cv-00980-CFC-JLH, Document 192, *Acera Surgical, Inc., Retectix, LLC, and Washington University*, Plaintiffs, v. *Nanofiber Solutions, LLC, Paragen Technologies LLC, Atreon Orthopedics LLC, and Renovoderm LLC*, Defendants, And Related Counterclaims, in 898 pages.

Joint Claim Construction Brief Regarding U.S. Pat. No. 11,224,677, filed Mar. 31, 2023, in Case No. 1:20-cv-00980-FCF-JLH, Document 191, *Acera Surgical, Inc., Retectix, LLC, and Washington University*, Plaintiffs, v. *Nanofiber Solutions, LLC, Paragen Technologies LLC, Atreon Orthopedics LLC, and Renovoderm LLC*, Defendants, and Related Counterclaims, in 86 pages.

Joint Claim Construction Chart, filed Mar. 30, 2023, in Case No. 1:20-cv-00980-CFC-JLH, Document 188, *Acera Surgical, Inc., Retectix, LLC, and Washington University*Plaintiffs, v. *Nanofiber Solutions, LLC, Paragen Technologies LLC, Atreon Orthopedics LLC, and Renovoderm LLC*, Defendants, and Related Counterclaims, in 39 pages.

Report and Recommendation filed Oct. 12, 2022, in Case No. 1:20-cv-00980-CFC-JLH, Document 147, *Acera Surgical, Inc., Retectix, LLC, and Washington University*, Plaintiffs, v. *Nanofiber Solutions, LLC, Paragen Technologies LLC, Atreon Orthopedics LLC, and Renovoderm LLC*, Defendants, and *Nanofiber Solutions, LLC, and The Research Foundation for the State University of New York*, Counterclaim Plaintiffs, v. *Acera Surgical, Inc.*, Counterclaim Defendant, in 24 pages.

Joint Claim Construction Brief, filed Jul. 29, 2022, in Case No. 1:20-cv-00980-CFC-JLH, Document 120, *Acera Surgical, Inc., Retectix, LLC, and Washington University*, Plaintiffs, v. *Nanofiber Solutions, LLC, Paragen Technologies LLC, Atreon Orthopedics LLC, and Renovoderm LLC*, Defendants, and Related Counterclaims, in 79 pages.

Joint Appendix to Claim Construction Brief filed Jul. 29, 2022, Document 121, in Case No. 1:20-CV- 00980-CFC-JLH, *Acera Surgical, Inc., Retectix, LLC, and Washington University*, Plaintiffs, v. *Nanofiber Solutions, LLC, Paragen Technologies LLC, Atreon Orthopedics LLC, and Renovoderm LLC*, Defendants, and Related Counterclaims, in 731 pages.

Joint Claim Construction Chart, filed May 10, 2022, Document 99, in Case No. 1:20-CV-00980-CFC-JLH, *Acera Surgical, Inc., Retectix, LLC, and Washington University*, Plaintiffs, v. *Nanofiber Solutions, LLC, Paragen Technologies LLC, Atreon Orthopedics LLC, and Renovoderm LLC*, Defendants, and Related Counterclaims, in 273 pages.

Joint Claim Construction Chart filed Feb. 7, 2023, Document 172, in Case No. 1:20-CV-00980-CFC-JLH, *Acera Surgical, Inc., Retectix, LLC, and Washington University*, Plaintiffs, v. *Nanofiber Solutions, LLC, Paragen Technologies LLC, Atreon Orthopedics LLC, and Renovoderm LLC*, Defendants, and Related Counterclaims, in 57 pages.

Plaintiffs Acera Surgical, Inc., Retectix, LLC and Washington University's Objections to the Report and Recommendation [D.I 147} filed Oct. 26, 2022, in Case No. 1:20-CV-00980-CFC-JLH, *Acera Surgical, Inc., Retectix, LLC, and Washington University*, Plaintiffs, v. *Nanofiber Solutions, LLC, Paragen Technologies LLC, Atreon Orthopedics LLC, and Renovoderm LLC*, Defendants, and Related Counterclaims, in 18 pages.

\* cited by examiner

NON-WOVEN GRAFT MATERIALS FOR NERVE REPAIR AND REGENERATION

CROSS-REFERENCE TO RELATED APPLICATIONS

The present application claims the benefit of U.S. Provisional Application No. 63/241,366, filed Sep. 7, 2021, which is hereby incorporated by reference in its entirety.

BACKGROUND

Field

The present disclosure relates generally to non-woven graft materials, which can be used for example in specialized surgical procedures, such as neurosurgical procedures, wound repair, oral surgery, dermal repair and regeneration, head and neck surgery, endonasal surgery and bone repair, methods for making the non-woven graft materials, and/or methods for repairing tissue such as neurological tissue using the non-woven graft materials.

SUMMARY

One or more embodiments described herein provide structures having a plurality of aligned (e.g., longitudinally or axially aligned) and non-aligned (e.g. randomly oriented) fibers. When such a structure is used as a biomedical patch, the alignment of fibers as described herein may provide directional cues that influence cell propagation. For example, the structures provided may promote new cell growth along the fibers, such that cell propagation in one or more desired directions may be achieved.

Aspects of the present disclosure relate generally to electrospun resorbable nerve products. In some embodiments, the nerve product may be a conduit, wrap, or graft. In particular, in some embodiments, the present disclosure relates to systems, devices, and methods for the production and application of an electrospun resorbable nerve product.

In some aspects, the present disclosure is directed to a resorbable non-woven graft material comprising: a first non-woven fiber composition, wherein the first fiber composition comprises a polymer selected from the group consisting of polycaprolactone, polydioxanone, poly (glycolic acid), poly(L-lactic acid), poly(lactide-co-glycolide), poly (L-lactide), poly(D,L-lactide), poly(ethylene glycol), montmorillonite, poly(L-lactide-co-ε-caprolactone), poly(ε-caprolactone-co-ethyl ethylene phosphate), poly [bis(p-methylphenoxy) phosphazene], poly(3-hydroxybutyrate-co-3-hydroxyvalerate), poly(ester urethane) urea, poly(p-dioxanone), polyurethane, polyethylene terephthalate, poly (ethylene-co-vinylacetate), poly(ethylene oxide), poly (phosphazene), poly(ethylene-co-vinyl alcohol), polymer nanoclay nanocomposites, poly(ethylenimine), poly(ethyleneoxide), poly vinylpyrrolidone, polystyrene (PS) and combinations thereof; and a second non-woven fiber composition, wherein the second fiber composition comprises a polymer selected from the group consisting of polycaprolactone, polydioxanone, poly (glycolic acid), poly(L-lactic acid), poly(lactide-co-glycolide), poly(L-lactide), poly(D,L-lactide), poly(ethylene glycol), montmorillonite, poly(L-lactide-co-ε-caprolactone), poly(ε-caprolactone-co-ethyl ethylene phosphate), poly [bis(p-methylphenoxy) phosphazene], poly(3-hydroxybutyrate-co-3-hydroxyvalerate), poly (ester urethane) urea, poly(p-dioxanone), polyurethane, polyethylene terephthalate, poly(ethylene-co-vinylacetate), poly(ethylene oxide), poly(phosphazene), poly(ethylene-co-vinyl alcohol), polymer nanoclay nanocomposites, poly(ethylenimine), poly(ethyleneoxide), poly vinylpyrrolidone; polystyrene and combinations thereof; and wherein the first fiber composition and the second fiber composition comprise different polymers.

One or more structures provided may be created using an apparatus that includes one or more first electrodes that define an area and/or partially circumscribe an area. For example, a single first electrode may enclose the area, or a plurality of first electrode(s) may be positioned on at least a portion of the perimeter of the area. A second electrode is positioned within the area. In exemplary embodiments, when the electrodes are electrically charged at a first polarity, and a spinneret dispensing a polymer (e.g., toward the second electrode) is electrically charged at a second polarity opposite the first polarity, the dispensed polymer forms a plurality of fibers extending from the second electrode to the first electrodes. Further, electrodes with rounded (e.g., convex) surfaces may be arranged in an array, and a fibrous structure created using such electrodes may include an array of wells at positions corresponding to the positions of the electrodes For purposes of this summary, certain aspects, advantages, and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

All of these embodiments are intended to be within the scope of the invention herein disclosed. These and other embodiments will become readily apparent to those skilled in the art from the following detailed description having reference to the attached figures, the invention not being limited to any particular disclosed embodiment(s).

BRIEF DESCRIPTION OF THE DRAWINGS

Features of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

DETAILED DESCRIPTION

Figure 1:
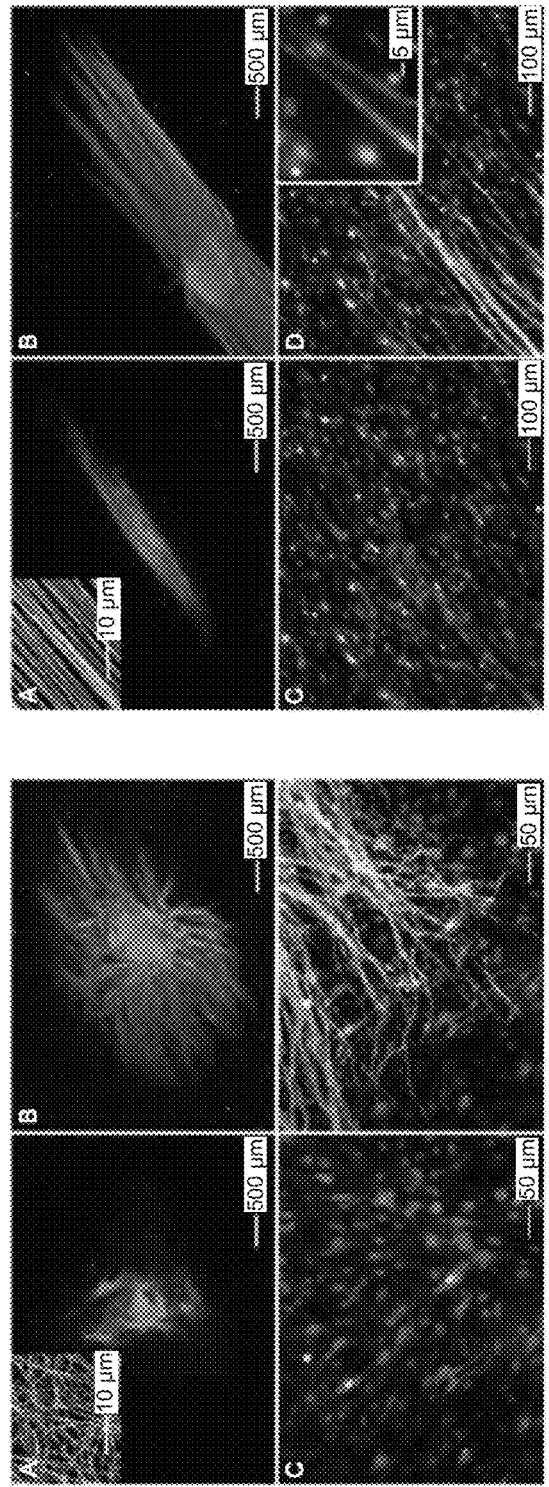
FIG. 1 depicts embodiments of nerve growth and regeneration patterns based on structured or unstructured underlying material.

The detailed description set forth below in connection with the drawings is intended as a description of various configurations and is not intended to represent the only configurations in which the concepts described herein may be practiced. The detailed description include specific details for the purpose of providing a thorough understanding of various concepts. However, it will be apparent to those skilled in the art that these concepts may be practiced without these specific details.

All patents, applications, published applications and other publications referred to herein are incorporated herein by reference to the referenced material and in their entireties. If a term or phrase is used herein in a way that is contrary to or otherwise inconsistent with a definition set forth in the patents, applications, published applications and other publications that are herein incorporated by reference, the use herein prevails over the definition that is incorporated herein by reference.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the scope of the disclosure as defined by the appended claims.

Definitions

All technical and scientific terms used herein have the same meaning as commonly understood to one of ordinary skill in the art to which this disclosure belongs unless clearly indicated otherwise.

As used herein, the singular forms "a", "and", and "the" include plural referents unless the context clearly dictates otherwise. Thus, for example, reference to "a sequence" may include a plurality of such sequences, and so forth.

The terms comprising, including, containing and various forms of these terms are synonymous with each other and are meant to be equally broad. Moreover, unless explicitly stated to the contrary, examples comprising, including, or having an element or a plurality of elements having a particular property may include additional elements, whether or not the additional elements have that property.

As used herein, the terms "nano-sized fibers" or "nanofibers" refer to very small diameter fibers having an average diameter not greater than 2000 nanometers, and suitably, not greater than 1500 nanometers (nm). Nanofibers are generally understood to have a fiber diameter range of about 10 to about 1500 nm, more specifically from about 10 to about 1000 nm, more specifically still from about 20 to about 500 nm, and most specifically from about 20 to about 400 nm. Other exemplary ranges include from about 50 to about 500 nm, from about 100 to 500 nm, or about 40 to about 200 nm.

As used herein the term "microfibers" refers to small diameter fibers having an average diameter not greater than 75 microns, for example, having an average diameter of from about 0.5 microns to about 50 microns, or more particularly, microfibers having an average diameter of from about 2 microns to about 40 microns. Another frequently used expression of fiber diameter is denier. The diameter of a polypropylene fiber given in microns, for example, may be converted to denier by squaring, and multiplying the result by 0.00629, thus, a 15 micron polypropylene fiber has a denier of about 1.42 (152×0.00629=1.415). As used interchangeably herein, "non-woven graft material" and "non-woven graft fabric" refer to a material having a structure of individual fibers or threads which are interlaid, but not in an identifiable manner as in a knitted fabric. Non-woven graft materials and non-woven graft fabrics can be formed from many processes such as for example, electrospinning processes, meltblowing processes, spunbonding processes, melt-spraying and bonded carded web processes. The basis weight of non-woven graft materials is usually expressed in ounces of material per square yard (osy) or grams per square meter (gsm) and the fiber diameters are usually expressed in nanometers and micrometers (microns). Suitable basis weight of non-woven graft materials of the present disclosure can range from about 50 gsm to about 300 gsm. More suitably, basis weight of non-woven graft materials of the present disclosure can range from about 70 gsm to about 140 gsm. The tensile strength of the non-woven graft material of the present disclosure can range from about 5 Newtons (N) to about 50 Newtons (N), including from about 1 N to about 10 N to about 15 N. The strength of the non-woven graft material of the present disclosure can also be described in terms of suture pull-out strength, which refers to the force at which a suture can be torn from the non-woven graft material. Suitable suture pull-out strength can range from about 1 N to about 5 N.

As used herein, the term "electrospinning" refers to a technology which produces nano-sized fibers referred to as electrospun fibers from a solution using interactions between fluid dynamics and charged surfaces. In general, formation of the electrospun fiber involves providing a solution to an orifice in a body in electric communication with a voltage source, wherein electric forces assist in forming fine fibers that are deposited on a surface that may be grounded or otherwise at a lower voltage than the body. In electrospinning, a polymer solution or melt provided from one or more needles, slots or other orifices is charged to a high voltage relative to a collection grid. Electrical forces overcome surface tension and cause a fine jet of the polymer solution or melt to move towards the grounded or oppositely charged collection grid. The jet can splay into even finer fiber streams before reaching the target and is collected as interconnected small fibers. Specifically, as the solvent is evaporating (in processes using a solvent), this liquid jet is stretched to many times it original length to produce continuous, ultrathin fibers of the polymer. The dried or solidified fibers can have diameters of about 40 nm, or from about 10 to about 100 nm, although 100 to 500 nm fibers are commonly observed. Various forms of electrospun nanofibers include branched nanofibers, tubes, ribbons and split nanofibers, nanofiber yarns, surface-coated nanofibers (e.g., with carbon, metals, etc.), nanofibers produced in a vacuum, and so forth. The production of electrospun fibers is illustrated in many publication and patents, including, for example, P. W. Gibson et al., "Electrospun Fiber Mats: Transport Properties," AIChE Journal, 45(1): 190-195 (January 1999), which is hereby incorporated herein by reference.

As used herein, the term "type" such as when referring to "different types of fibers" or "distinct types of fibers" refers to fibers having "a substantially different overall material composition" with measurably different properties, outside of "average diameter" or other "size" differences. That is, two fibers can be of the same "type" as defined herein, yet have different "average diameters" or "average diameter ranges." Although fibers are of different "types" when they have a substantially different overall material composition, they can still have one or more components in common. For example, electrospun fibers made from a polymer blend with a first polymeric component present at a level of at least 10 wt % would be considered a different fiber type relative to electrospun fibers made from a polymer blend that was substantially free of the first polymeric component. Fibers of different "types" can also have a completely different content, each made of a different polymer for example, or one made from a polymer fiber and the other from a titania fiber, or a ceramic fiber and a titania fiber, and so on.

As used herein the term "polymer" generally includes but is not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configuration of the material. These configurations include, but are not limited to isotactic and atactic symmetries.

The fiber compositions used in the present disclosure can be produced from any resorbable material that meets the criteria of that material as those criteria are described above. The fiber compositions can be formed from resorbable polymers such as (but not limited to) polymers of lactic and glycolic acids, copolymers of lactic and glycolic acids, poly(ether-co-esters), poly(hydroxybutyrate), polycaprolactone, copolymers of lactic acid and ε-aminocapronic acid, lactide polymers, copolymers of poly(hydroxybutyrate) and 3-hydroxyvalerate, polyesters of succinic acid, poly(N-acetyl-D-glucosamine), polydioxanone, cross-linked hyaluronic acid, cross-linked collagen, and the like, and combinations thereof. Suitable synthetic polymers can be, for example, polycaprolactone (poly(ε-caprolactone), PCL), polydioxanone (PDO), poly (glycolic acid) (PGA), poly(L-lactic acid) (PLA), poly(lactide-co-glycolide) (PLGA), poly (L-lactide) (PLLA), poly(D,L-lactide) (P(DLLA)), poly(ethylene glycol) (PEG), montmorillonite (MMT), poly(L-lactide-co-ε-caprolactone) (P(LLA-CL)), poly(ε-caprolactone-co-ethyl ethylene phosphate) (P(CL-EEP)), poly [bis(p-methylphenoxy) phosphazene] (PNmPh), poly (3-hydroxybutyrate-co-3-hydroxyvalerate) (PHBV), poly (ester urethane) urea (PEUU), poly(p-dioxanone) (PPDO), polyurethane (PU), polyethylene terephthalate (PET), poly (ethylene-co-vinylacetate) (PEVA), poly(ethylene oxide) (PEO), poly(phosphazene), poly(ethylene-co-vinyl alcohol), polymer nanoclay nanocomposites, poly(ethylenimine), poly(ethyleneoxide), poly vinylpyrrolidone; polystyrene (PS) and combinations thereof. Particularly suitable polymers include poly(lactic-co-glycolic acid), polydioxanone, polycaprolactone, and combinations thereof. In some embodiments, the fiber compositions can be formed from one or more populations consisting of PEO and PEG.

The fibers for the fiber compositions may be of a variety of sizes as deemed suitable by one skilled in the art for the end purpose of the non-woven graft material. Typically, the fibers have a mean fiber diameter of less than 5 μm, including less than 2 μm, including less than 1.5 μm, and including less than 1.0 μm. For example, in some embodiments, the fibers can have a mean fiber diameter ranging from about 10 nm to about 5 μm, more specifically from about 10 nm to about 1.0 μm, more specifically still from about 20 nm to about 500 nm, and most specifically from about 20 nm to about 400 nm. Other exemplary ranges include from about 50 nm to about 500 nm, from about 100 nm to about 500 nm, and about 40 nm to about 200 nm.

Suitable ratios of the first fiber composition to the second fiber composition resulting in the non-woven graft material can range from about 10 to 1 to about 1 to 10.

SUMMARY

The present disclosure relates generally to non-woven graft materials, which can be used for example in specialized surgical procedures, such as neurosurgical procedures, wound repair, oral surgery, dermal repair and regeneration, head and neck surgery, endonasal surgery and bone repair, methods for making the non-woven graft materials, and methods for repairing tissue such as neurological tissue using the non-woven graft materials.

Aspects of the present disclosure relate generally to electrospun resorbable nerve products. In some embodiments, the nerve product may be a conduit, wrap, or graft. In particular, in some embodiments, the present disclosure relates to systems, devices, and methods for the production and application of an electrospun resorbable nerve product.

In some embodiments, the present disclosure may be related to electrospun nerve conduits, wraps, or grafts. Electrospun nerve conduits, wraps, or grafts may be comprised out of a plurality of flexible, hollow resorbable poly(lactide-co-ε-caprolactone) tubes designed to provide a protective environment for peripheral nerve regeneration after injury and to create a conduit to guide axonal growth across a nerve gap. In some embodiments, the conduits, wraps, or grafts may incorporate longitudinally or axially aligned fibers on the inner lumen of the conduits, wraps, or grafts and randomly aligned fibers on the outer lumen of the conduits, wraps, or grafts. In some embodiments, conduits, wraps, or grafts may be constructed out of poly(lactide-co-ε-caprolactone). In some embodiments, the conduits, wraps, or grafts may possess suitable handling and mechanical properties for surgical use. In some embodiments, the conduits, wraps, or grafts may demonstrate a suitable tensile strength for surgical implantation, as well as suitably high suture retention strength to facilitate sutured coaptation to a transected nerve. In some embodiments, the conduits, wraps, or grafts may also possess sufficient wall strength so as not to collapse under tissue compression following implantation.

INTRODUCTION

Every year, roughly twenty million Americans suffer from peripheral nerve injury caused by trauma and medical disorders, and these nerve injuries result in approximately $150 billion spent in annual health-care dollars in the United States. The majority of peripheral nerve injuries typically occur in the upper limb and are from traumatic causes. Severe nerve injury often leads to sensory and motor function defects that can result in complete paralysis of the affected limb or development of debilitating neuropathic pain. The primary goal of nerve repair can be to facilitate effective regeneration of the injured nerve and reinnervation of distal motor and sensory end organs needed for recovery of sensorimotor function.

In particular, nerve injury can involve one or more transected nerves. When a nerve is transected, surgical repair can often be required. Generally speaking, the greater the gap length between the ends of the transected nerve, the more challenging the repair. Additionally, larger gap lengths can be associated with reduced sensorimotor outcomes. In fact, gap segment length can be the most important factor in deciding which technique or device to use in a repair. For example, severed nerves can be directly repaired if the nerve ends are close together (<8.9 mm gap) and require no tension on the nerve to reconnect. These can be called "short gap" or "no gap" injuries. In some instances, repairs often include approximating the nerve ending margins with suture. Protective wraps or coaptation aids may be used to strengthen the repair. Given the likely stress on a repaired nerve (from local tissue swelling, vascular supply compromises, flexion/extension of anatomy), the direct repair of damaged nerve ends is typically infrequent and risks poor sensorimotor outcomes. Larger gap nerve injuries can require a "bridging" material to reconnect the transected ends of an injured nerve across the nerve gap. These interventions can be required both in instance of short gap and long gap injuries where the surgeon feels it is too risky to join the nerve endings with suture. Wraps, conduits, and/or grafts, such as some embodiments described herein, may be used in these types of surgeries.

In addition, nerve injury can also involve crushed and/or compressed nerves. In injuries where the nerve is not transected and the nerve ultrastructure is still intact, surgical repair is typically less common. However, in severe cases, surgery may be needed to reduce pressure and inflammation while protecting the nerve. Nerve wraps, such as those described herein, may be utilized to protect the nerve while it heals, providing a barrier from surrounding tissue. Compression injuries, where blood supply and nerve structure in still intact, can have a greater likelihood of complete sensorimotor recovery.

Of the injuries that require surgical nerve reconstruction, approximately 560K can require and/or benefit from the use of nerve grafts, wraps or coverings, such as one or more embodiments described herein. 55% of these (~307K) can be considered "no gap" procedures, where the size of the gap is less than 8.9 mm; and the remainder can be considered gap procedures, resulting in a gap greater than 9 mm.

Generally speaking, there can be three types of biomaterial-based devices for nerve repair. For example, in some embodiments, conduits are comprised of collagen or synthetic materials and can be used to connect transected nerve ends and guide regenerating nerve fibers from the proximal nerve stump to the distal nerve stump. These devices can be deployed by grossly aligning the fascicles in the proximal and distal nerve stumps and then suturing the nerve stumps in to either end of the conduit, thereby eliminating potential stress on the nerve. In some embodiments, conduits are used for very short gaps (20 mm or less) due to the lack of structural support for regenerating axons and the inability of conduits to successfully bridge larger nerve gaps. In addition, in some embodiments, wraps can be used to protect the nerve while healing, provide a barrier from surrounding tissue, or to strengthen the repair. Moreover, in some embodiments, allografts can be human cadaveric nerve tissue that has been chemically processed to remove all donor cells and then terminally sterilized. The processed acellular nerve allograft can be used to repair and reconnect the damaged nerve by suturing the graft end to end with the transected nerve stumps.

However, peripheral nerve injuries are challenging clinical problems that commonly result in permanent sensorimotor deficits despite the use of the most advanced surgical interventions. In other words, current products and/or clinical approach may not fully address clinical needs, the shortcomings of which some embodiments described herein address.

In particular, microsurgical repair of injured nerves utilizing the patient's own harvested nerve tissue can represent the clinical gold-standard; however, this can be limited by graft availability and permanent nerve damage at the site of graft harvest. Furthermore, autograft repair may only support substantial sensorimotor recovery in roughly 50% of patients, particularly those with small gap rather than large gap injuries. Apart from the patient's own harvested nerve tissue, few clinical options currently exist for repairing damage nerve. Multiple synthetic and xenogenic nerve conduits and wraps have been developed but are only effective in repairing small gap injuries, unlike some embodiments described herein. In particular, existing decellularized nerve allograft products, while showing improvement over existing nerve conduits, demonstrated questionable performance in long gap settings. As a result, new and improved solutions for peripheral nerve repair capable of improving the speed and quality of functional nerve regeneration in both small and large gap injuries are needed. Some embodiments described herein address such technical shortcomings and needs.

Generally speaking, small and large gap injuries are typically most commonly repaired utilizing harvested nerve autografts due to ability to achieve superior clinical outcomes. Autograft repair can involve harvesting a nerve from the patient's own body (often the leg), thereby requiring 2 surgeries/incisions and inducing donor site morbidity at the harvest site. This donor nerve may be utilized directly to repair the nerve defect by suturing the graft end to end with the transected nerve stumps, or in cases involving repair of larger diameter nerves, may be bundled together to create a larger graft for use in repairing the damaged nerve.

Typically, human autografts can be preferred as autografting can be superior to nerve conduits for longer gaps (>3 cm), more proximal injuries, and critical nerves. Autograft repair can represent the current gold-standard treatment for peripheral nerve injuries and offers a 50.5-81.6% recovery rate. However, donor site morbidity at the site of nerve harvest can result in permanent sensory deficits.

In some embodiments, nerve grafts can be single, cable, trunk, interfascicular, or vascularized. In some embodiments, a single graft can join nerve gaps with a segment of a donor nerve of similar diameter. In some embodiments, to span gaps between large diameter nerves, cable grafts can be used, comprising multiple lengths of a smaller diameter donor nerve to approximate the diameter of the injured nerve. In some embodiments, donor nerve grafts are harvested from expendable sensory nerves including the sural and medial antebrachial and are reversed in orientation to maximize the number of axons successfully regenerating through the graft by funneling them distally. In some embodiments, this can prevent loss of regenerating axons downside branches of the donor nerve graft.

In some instances, human cadaveric nerve allografts can be used in a limited number of patients with extensive nerve injuries and inadequate autologous nerve donor tissue. In some embodiments, compared to autografts there are no donor supply limitations or donor site morbidity; however, there can be significant costs and complexity with their use. For example, early human nerve allografts were used without decellularization. In these cases, donor Schwann cells within the nerve allografts may display major histocompatibility complexes and incited a T-cell response. Therefore, recipients may be immunosuppressed for up to two years until the donor nerve graft has been repopulated with host Schwann cells.

In some embodiments, recent advancement in decellularization techniques employing chemical detergents, enzymatic degradation, and irradiation can allow for the production of decellularized nerve allografts with no requirements for immunosuppression. For example, a nerve allograft product can be configured for use in short and long graft repair scenarios. In some embodiments, the processed and sterilized cadaveric nerve allografts preclude the need for autologous nerve harvesting, increasing off-the-shelf availability of nerve graft material and eliminating donor site morbidity. Allograft repair can demonstrate positive clinical outcomes particularly in small gap injuries <30 mm.

However, in some instances, the acellular nerve allograft can demonstrate inconsistent clinical performance when utilized to repair nerve gaps >30 mm. Unlike nerve autografts, the decellularized nerve allograft can lack autologous cells critical to axonal regeneration. Specifically, in some instances, the absence of autologous Schwann cells, extracellular matrix proteins, and growth factors can reduce the ability of processed nerve allografts to support nerve regeneration over long distances. Clinical studies have demonstrated that sensory, mixed, and motor nerves repaired with short acellular nerve allograft recovered at 88.6%, 77%, and 85.7%, respectively. Further, the efficacy of the graft in various nerve gap lengths and showed that short (5 to 14 mm) recovered at 100%, medium (15 to 29 mm) recovered at 76.2%, and long (30 to 50 mm) recovered at 90.9% (mean follow up 265-279 d). Yet, alternate studies suggest that acellular nerve allografts do not perform equivalent to nerve autograft, particularly in long nerve gap injuries. As a result, surgeon confidence with allografts in long gap repairs remains low and new and improved solutions are needed.

Generally speaking, the advantage of acellular nerve allografts over hollow nerve conduits can be that the internal nerve structure including endoneurial tubes, basal lamina, and laminin remain intact, facilitating axonal regeneration. A recent level III study demonstrated functional recovery for injuries with gaps between 5 and 50 mm. However, the majority of their clinical use has been limited to small sensory nerves, for example, digital nerves, for gaps less than 3 cm. Decellularized nerve grafts or nerve conduits may be not considered a replacement for autologous nerve grafting in motor nerves, gaps more than 3 cm, or in proximal nerve injuries. This is because certain allografts are typically prepared with detergents, ChABC enzyme optimized to remove axon-inhibiting proteins and encourage axonal regeneration. Axonal regeneration can only progress/extend a limited distance with the organized and concerted support of active Schwann cells. Certain allograft may not adequately attract/support Schwann cell infiltration, resulting in an "unsupportive dead zone" in the middle of the graft. There remains a significant need for effective alternatives to nerve autograft repair in the setting of long gap injuries, including those optimized for Schwann cell infiltration. Some embodiments described herein address such technical shortcomings.

In addition, in some embodiments, conduits and/or wraps are provided. Existing conduits have failed to demonstrate equivalent or superior outcomes to autografts for gaps greater than 3 cm. Conduits can be categorized as autogenous biological, non-autogenous biological, or nonbiological. In some embodiments, autogenous biological conduits can include hollow vein and arterial conduits and soft tissues, including muscle and tendon grafts. The concern with muscle grafts is that regenerating axons are not contained within the graft and may form neuromas or aberrant regeneration. Vein conduits are the most popular biological conduits and prospective study of twenty-two patients with defects of <3 cm in the hand and forearm, finding that autogenous vein nerve conduits produced results comparable to sural nerve digital grafts. In some embodiments, the use of vein grafts may be reserved for small, less functional nerves with small nerve gaps (e.g., digital sensory nerves with less than a 3 cm gap).

In addition, in some embodiments, nonautogenous biological conduits are provided. In some embodiments, non-autogenous biological conduits have been made from collagens type I, III, or IV and are available in clinical settings. Animal studies with collagen conduits have demonstrated equivalent efficacy when compared with autograft; however, comprehensive clinical studies are lacking. In some embodiments, second generation resorbable nonbiological conduits are made from polyglycolic acid (PGA), polylactic acid (PLA), or poly lactide-co-glycolide acid (PLGA). In some instances, nonresorbable conduits including silicone and Gore-Tex demonstrated unwanted effects including axonal compression during regeneration and fibrous foreign body reaction. PGA nerve conduits have been assessed by a number of clinical studies and demonstrate equivalent results to nerve repairs or autologous grafts for short or moderate digital nerve gaps.

Extensive research continues to focus on adding internal structure, Schwann cells, and growth factors to support axonal regeneration. A prospective trial compared vein grafts to PGA conduits in sensory nerve gaps of 4-25 mm that demonstrated equivalent cost and sensory outcomes at 12 months. In some instances some autologous nerve graft alternatives including decellularized nerve grafts and autogenous and nonautogenous conduits can demonstrate similar efficacy but their use may be limited to sensory nerves with small gaps <3 cm. Primary nerve repair or autogenous nerve grafts can be used for surgical nerve reconstruction for severe nerve injuries.

In some instances, nerve conduits have demonstrated clinical success in short gap injuries. An analysis of median and ulnar nerve repairs demonstrated that 51.6% achieve satisfactory motor recovery (M4-5), with (42.6%), experiencing satisfactory sensory recovery (S3+ to S4). Younger age and more distal injuries may have better outcomes, although many articles report higher rates of "good" motor outcomes using a lower cutoff (M3—movement against gravity only). In some embodiments, use of synthetic nerve conduits have demonstrated an improvement over early technique. Clinical use of ePTFE conduits in 43 patients exhibiting median and ulnar nerve gaps ranging from 1.5 to 6 cm was reported. Patients with smaller gaps (up to 4 cm) had significantly improved outcomes vs larger gaps (78.6% vs 13.3% functional recovery). In some embodiments, xenogenic collagen conduits were utilized in a prospective series of 22 digital nerve repairs and achieved excellent or good sensory outcomes in only 15 of 22 (68%) of subjects. The xenogenic collagen study only focused on small nerve gaps and excluded nerve gaps greater than 20 mm. In a larger study of 126 nerve injuries in 96 patients, nerve injuries were repaired with a xenogenic collagen conduit with an average nerve gap of 12.8 (range 2.5 to 20 mm). In this cohort, nerve function recovery was only observed in 43% of subjects. In total, these results demonstrate both the opportunity for improvement in the speed and quality of functional recovery both in small gap and large gap injuries. Some embodiments described herein address such technical shortcomings.

Electrospun Hybrid-Scale Fibers

Electrospun hybrid-scale fibers represent a new class of synthetic nanomaterials with the capability to mimic the hierarchical structure of the extracellular matrix (ECM). Most importantly, electrospun nanofibers can be readily collected as uniaxially aligned arrays, providing topographical cues to direct and enhance axonal extension during regeneration. In some embodiments, by controlling size, alignment, and stacking, scaffolds made of electrospun hybrid-scale fibers can be easily adapted for direct implantation. These unique features can make electrospun hybrid-scale fibers an intriguing class of scaffolds with unique applications in neural tissue engineering. Hybrid-scale nanofibers include fibers at various dimensional scales, including microscale fibers, nanoscale fibers, and other fiber populations.

Nerve Conduit

In some embodiments, a fully-synthetic nanofiber nerve conduit comprised of two layers of electrospun nanofibers rolled into a tube, with the inner and outer layers containing uniaxially aligned and randomly aligned fibers, respectively is provided. In some embodiments, randomly oriented nanofibers provided an isotropic mechanical property for the NGC (nerve graft conduit) and render the conduit suturable and tear-resistant during surgical implantation. In some embodiments, aligned nanofibers served the role of guiding and supporting regenerating axons into the distal nerve stump via topographical cues. Prior studies demonstrated the success of NGCs comprised of aligned nanofibers to enhance axonal regeneration, yet also demonstrated the need to enhance the handling and suturability of the graft through the addition of a reinforcing layer of nanofibers. In some instances, random fibers were added to the outside of the aligned fiber layer to provide additional mechanical support without compromising the guidance cues presented to the axons extending through the inner lumen of the conduit. In some embodiments, the bi-layer electrospun construction, and integration of aligned nanofibers presenting topographical contact cues may enhance overall neuronal repair.

In some embodiments, in order to demonstrate the ability of a bi-layer nanofiber conduit to enhance and direct both axonal regeneration and Schwann cell migration a cell culture model was utilized (FIG. 1). Bundles of neurons, known as dorsal root ganglia (DRG), were utilized as a model system to demonstrate how neurite outgrowth occurs on (i) a pristine double-layered scaffold, with uniaxially aligned and random fibers in the top and bottom layers, respectively, and (ii) a double-layered scaffold pre-seeded with primary Schwann cells, a type of glial cell in the PNS. In some instances, aligned nanofiber matrices supported neurite extension from DRG in both the absence and presence of pre-seeded Schwann cells. In both cases extending neurites were observed to project from the neuronal cell bodies and run parallel to the electrospun fibers on the inner surface of the scaffold. In some instances, this behavior is significantly different than that of cell bodies placed on randomly oriented nanofiber scaffolds, and demonstrates that aligned nanofiber are able to spatially guide extending axons along the length of the conduit toward the distal nerve stump. In some embodiments, the studies also demonstrated that the aligned nanofiber were also able to support and orient Schwann cells, a critical supporting cell type necessary for successful nerve regeneration. FIG. 1 illustrates neuronal growth patterns on a variety of substrates. Unstructured materials encourage disorganized axonal growth with no or little alignment of supporting schwann cells (SCs). In comparison, patterned nanofiber materials encouraged organized axonal growth and alignment of supporting SCs, leading to nearly 10× increase in nerve regeneration. In some embodiments, successful seeding of Schwann cells on to the surface of the nanofiber conduit demonstrate the ability of the conduit to support Schwann cell infiltration and further enhance axonal elongation through the conduit. In some instances, in vitro studies confirmed the ability of the nanofiber conduit to support neurite outgrowth, direct and enhance axonal elongation, and support Schwann cell infiltration capable of further enhancing nerve regeneration.

Figure 2:
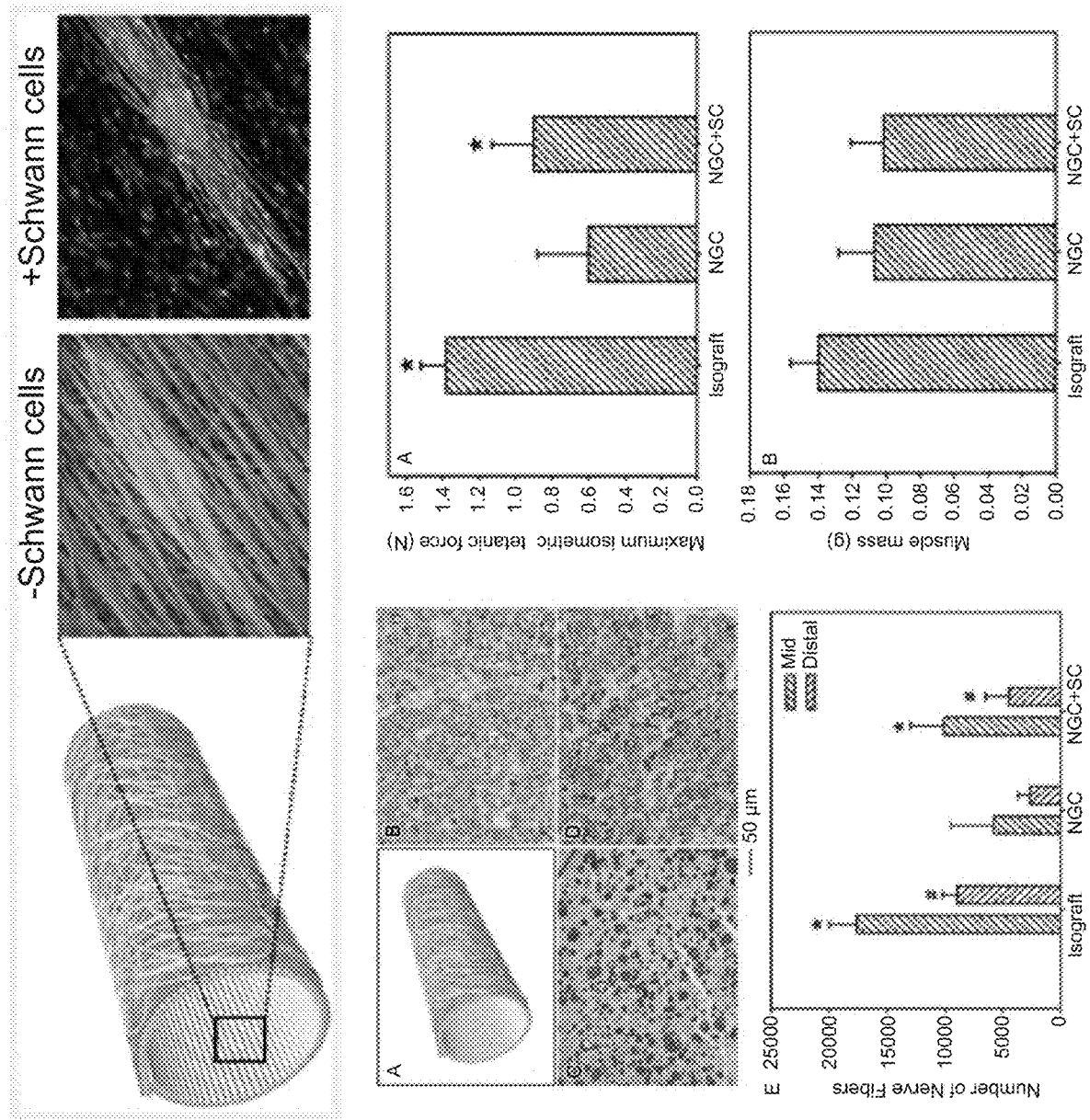
FIG. 2 illustrates a set of graphs and cell morphologies for nerve cells.

In some instances, an in vivo sciatic nerve transaction/repair model was utilized. Rats were anesthetized prior to surgical exposure of the right sciatic nerve through a dorsolateral gluteal muscle-splitting incision. The sciatic nerve was transected 5 mm proximal to the trifurcation to create a critical 14 mm nerve gap injury. The sciatic nerve was then repaired with either a 14 mm reversed nerve autograft (Isograph), a 16 mm electrospun nanofiber conduit (NGC), or a 16 mm electrospun nanofiber conduit pre-seeded with Schwann cells (NGC+SC) (See FIG. 2). Nerve grafts and conduits were microsurgically sutured to the proximal and distal nerve stumps using one 10-0 nylon suture and secured with fibrin sealant. Recipient nerves in all groups were challenged with a consistent 14 mm nerve gap. Following implantation, muscle fascia and skin were closed in two layers and animals were allowed to recover. Twelve weeks post-operatively, all animals were anesthetized and in situ electrophysiological testing of the regenerated nerve was performed. Additionally, functional recovery was assessed via measurement of evoked muscle force distal to the nerve repair site. Following testing, all animals were euthanized and the entire sciatic nerve was explanted for histomorphometric analysis and assessment of the quality of regenerated nerve tissue. In some embodiments, the in vivo testing demonstrated that the electrospun nanofiber conduit successfully repaired the critical nerve injury in the rodent nerve and facilitated successful reinnervation of distal musculature (FIG. 2). Histomorphological examination of regenerated nerve segments further demonstrated that the electrospun nanofiber conduits successfully supported axonal regeneration across the nerve gap and into the distal nerve stump. In some instances, the electrospun nanofiber conduit pre-seeded with autologous Schwann cells also highlights the future potential of the device to serve as a vehicle for pro-regenerative factors, such as chemotrophic growth factors (GDNF, BDNF, NGF, etc.) or stem cells.

In some embodiments, presented herein is an electrospun nerve conduit device comprised of fully resorbable polymeric fibers. In some embodiments, the electrospun nerve conduit device comprises a hollow tube of various diameters and lengths. In some embodiments, the hollow tube may comprise an inner and outer surface. In some embodiments, the inner surface of the tube may be comprised of longitudinally aligned hybrid-scale fibers structures which may direct and enhance nerve fiber regeneration and elongation. In some embodiments, aligned fiber matrices may improve axonal elongation up to 800% over conventional unorganized matrices. In some embodiments, the outer layer of the conduit may be comprised of randomly organized fibers in order to provide adequate suture strength and handling properties. In some embodiments, the electrospun nerve conduit device may be provided in terminally sterilized in a double peel foil pouches. In some embodiments, the electrospun nerve conduit device comprise a blend of PCL and PGA. In some embodiments, the aligned hybrid-scale fibers structures may increase the rate of infiltration of supporting cell types. In some embodiments, the supporting cell types are Schwann cells. In some embodiments, the electrospun synthetic nerve graft conduit is shelf stable. In some embodiments, no secondary site morbidity exists when the electrospun synthetic nerve conduit device is applied.

In some embodiments, the electrospun nerve conduit device may possess an inner diameter of 1.5 mm, with a length of 24 mm. In some embodiments, the electrospun nerve conduit device may possess an inner Core Length of 20 mm, such that there is a 2 mm Outer Lumen overhang on either side. In some embodiments, the geometry of the electrospun nerve conduit device may be tubular. In some embodiments, the fiber alignment of the electrospun nerve conduit device may comprise longitudinally or axially aligned fibers on the inner lumen of the tube, and randomly aligned fibers on the outer lumen of the tube. In some embodiments, the total wall thickness may range from 325 microns to 550 microns. In some embodiments, the outer lumen is comprised of randomly aligned fibers. In some embodiments, the outer lumen should represent at least 75% of the cross-sectional thickness. In some embodiments, the mean fiber diameter is less than 2 microns. In some embodiments, the mean pore area of the outer lumen is less than 300 microns. In some embodiments of the electrospun nerve conduit device, resorption and mass loss is 50% at 24 weeks. In some embodiments of the electrospun nerve conduit device, resorption and mass loss is 100% at 50 weeks. In some embodiments of the electrospun nerve conduit device, strength loss is 100% at 10 weeks. In some embodiments, the mean tensile strength is greater than 15 newtons. In some embodiments, the minimum tensile strength is greater than 10.5 newtons. In some embodiments, the mean suture retention strength is greater than 3 newtons. In some embodiments, the minimum suture retention strength may be greater than 1 newton. In some embodiments, the electrospun nerve conduit device may withstand compressive forces greater than 0.25 newtons without collapsing.

Nerve Wrap

In some embodiments, presented herein is an electrospun nerve wrap device comprised of fully resorbable polymeric fibers. In some embodiments, the electrospun nerve wrap device comprises a hollow tube of various diameters and lengths. In some embodiments, the hollow tube may comprise an inner and outer surface. In some embodiments, the inner surface of the tube may be comprised of longitudinally aligned hybrid-scale fibers structures which may direct and enhance nerve fiber regeneration and elongation. In some embodiments, aligned fiber matrices may improve axonal elongation up to 800% over conventional unorganized matrices. In some embodiments, the outer layer of the wrap may be comprised of randomly organized fibers in order to provide adequate suture strength and handling properties. In some embodiments, the electrospun nerve wrap device may be provided in terminally sterilized in a double peel foil pouches. In some embodiments, the electrospun nerve wrap device comprise a blend of PCL and PGA. In some embodiments, the aligned hybrid-scale fibers structures may increase the rate of infiltration of supporting cell types. In some embodiments, the supporting cell types are Schwann cells. In some embodiments, the electrospun nerve wrap device may comprise a slit cut along the outer surface. In some embodiments, the wrap may be utilized to protect and insure coaptation sites between the native nerve or donor nerve or nerve conduits or nerve grafts. In some embodiments, the electrospun nerve wrap device is placed on the nerve coaptation site after suturing or fixation has occurred. In some embodiments, the electrospun nerve wrap device may be wrapped around the nerve to protect the suture/fixation site and guide extending nerve fibers into the distal nerve stump and prevent axons from growing out into surrounding tissue. In some embodiments, the electrospun synthetic nerve wrap device is shelf stable. In some embodiments, no secondary site morbidity exists when the electrospun synthetic nerve wrap device is applied.

In some embodiments, the electrospun nerve wrap device may possess an inner diameter of 1.5 mm, with a length of 24 mm. In some embodiments, the electrospun nerve wrap device may possess an inner Core Length of 20 mm, such that there is a 2 mm Outer Lumen overhang on either side. In some embodiments, the geometry of the electrospun nerve wrap device may be tubular. In some embodiments, the fiber alignment of the electrospun nerve wrap device may comprise longitudinally or axially aligned fibers on the inner lumen of the tube, and randomly aligned fibers on the outer lumen of the tube. In some embodiments, the total wall thickness may range from 325 microns to 550 microns. In some embodiments, the outer lumen is comprised of randomly aligned fibers. In some embodiments, the outer lumen should represent at least 75% of the cross-sectional thickness. In some embodiments, the mean fiber diameter is less than 2 microns. In some embodiments, the mean pore area of the outer lumen is less than 300 microns. In some embodiments of the electrospun nerve wrap device, resorption and mass loss is 50% at 24 weeks. In some embodiments of the electrospun nerve wrap device, resorption and mass loss is 100% at 50 weeks. In some embodiments of the electrospun nerve wrap device, strength loss is 100% at 10 weeks. In some embodiments, the mean tensile strength is greater than 15 newtons. In some embodiments, the minimum tensile strength is greater than 10.5 newtons. In some embodiments, the mean suture retention strength is greater than 3 newtons. In some embodiments, the minimum suture retention strength may be greater than 1 newton. In some embodiments, the electrospun nerve wrap device may withstand compressive forces greater than 0.25 newtons without collapsing.

Nerve Graft

In some embodiments, presented herein is an electrospun synthetic nerve graft device comprised of a 3D matrix of aligned resorbable polymeric fibers. In some embodiments, the electrospun synthetic nerve graft device comprises a cylinder or cable, available in various diameters and lengths. In some embodiments, the electrospun synthetic nerve graft device is comprised polymeric fibers and mimics the aligned structure and architecture of native nerve tissue. In some embodiments, the outer surface of the electrospun synthetic nerve graft device may be comprised of a layer of randomly organized fibers that will mimic the epineurium and provide adequate suture strength and handling properties. In some embodiments, the cross-sectional area of the electrospun synthetic nerve graft device may be composed of a 3D matrix of highly-porous, longitudinally aligned resorbable hybrid-scale fibers. In some embodiments, the electrospun synthetic nerve graft device may mimic the structure and architecture of endoneurial tubes. In some embodiments, the electrospun synthetic nerve graft device is shelf stable. In some embodiments, no secondary site morbidity exists when the electrospun synthetic nerve graft device is applied.

In some embodiments, presented herein is an electrospun nerve graft device comprised of fully resorbable polymeric fibers. In some embodiments, the electrospun nerve graft device comprises a hollow tube of various diameters and lengths. In some embodiments, the hollow tube may comprise an inner and outer surface. In some embodiments, the inner surface of the tube may be comprised of longitudinally aligned hybrid-scale fibers structures which may direct and enhance nerve fiber regeneration and elongation. In some embodiments, aligned fiber matrices may improve axonal elongation up to 800% over conventional unorganized matrices. In some embodiments, the outer layer of the graft may be comprised of randomly organized fibers in order to provide adequate suture strength and handling properties. In some embodiments, the electrospun nerve graft device may be provided in terminally sterilized in a double peel foil pouches. In some embodiments, the electrospun nerve graft device comprise a blend of PCL and PGA. In some embodiments, the aligned hybrid-scale fibers structures may increase the rate of infiltration of supporting cell types. In some embodiments, the supporting cell types are Schwann cells.

In some embodiments, the electrospun nerve graft device may possess an inner diameter of 1.5 mm, with a length of 24 mm. In some embodiments, the electrospun nerve graft device may possess an inner Core Length of 20 mm, such that there is a 2 mm Outer Lumen overhang on either side. In some embodiments, the geometry of the electrospun nerve graft device may be cylindrical. In some embodiments, the fiber alignment of the electrospun nerve graft device may comprise longitudinally or axially aligned fibers on the inner lumen of the tube, and randomly aligned fibers on the outer lumen of the cylinder. In some embodiments, various densities may be represented throughout the longitudinally or axially aligned fibers throughout the cross section of the cylinder. In some embodiments, the cylinder may comprise three regions of differing densities of fibers. In some embodiments, the total wall thickness may range from 250 microns to 400 microns. In some embodiments, the outer lumen is comprised of randomly aligned fibers. In some embodiments, the outer lumen should represent at least 75% of the cross-sectional thickness. In some embodiments, the mean fiber diameter is less than 2 microns. In some embodiments, the mean pore area of the outer lumen is less than 300 microns. In some embodiments of the electrospun nerve graft device, resorption and mass loss is 50% at 24 weeks. In some embodiments of the electrospun nerve graft device, resorption and mass loss is 100% at 50 weeks. In some embodiments of the electrospun nerve graft device, strength loss is 100% at 10 weeks. In some embodiments, the mean tensile strength is greater than 15 newtons. In some embodiments, the minimum tensile strength is greater than 10.5 newtons. In some embodiments, the mean suture retention strength is greater than 3 newtons. In some embodiments, the minimum suture retention strength may be greater than 1 newton. In some embodiments, the electrospun nerve graft device may withstand compressive forces greater than 0.25 newtons without collapsing.

Example Embodiments

In some embodiments, any of the following arrangements are contemplated herein:

A resorbable hybrid-scale fiber matrix for use in facilitating nerve repair and regeneration.

In some embodiments, the resorbable hybrid-scale fiber matrix having a shape/geometry selected from a group of consisting of a tube, a conduit, a graft, a wrap, or a spiral wrap.

In some embodiments, the resorbable hybrid-scale fiber matrix being comprised of hybrid-scale fibers composed of a resorbable polymer selected from a group of polymers consisting of polycaprolactone, polylactic acid, polyglycolic acid, polydioxanone, poly(3-hydroxybutyrate-co-3-hydroxyvalerate), polyethylene oxide, polyethylene glycol, and combinations thereof.

In some embodiments, the resorbable hybrid-scale fiber matrix being comprised of hybrid-scale fibers composed of biologically derived and natural materials selected from a group of materials consisting of collagen, elastin, laminin, fibrin, etc.

In some embodiments, the resorbable hybrid-scale fiber matrix wherein the hybrid-scale fibers are formed via method of manufacturing selected from a group of methods consisting of electrospinning, melt electrospinning, force spinning, melt blowing, solvent casting, or combinations thereof.

In some embodiments, the resorbable hybrid-scale fiber matrix wherein a portion of the hybrid-scale fibers are uniaxially or longitudinally aligned, and a portion of the hybrid-scale fibers are randomly aligned.

In some embodiments, the resorbable hybrid-scale fiber matrix wherein the matrix is comprised of 2 or more layers of hybrid-scale fibers.

In some embodiments, the resorbable hybrid-scale fiber matrix wherein the hybrid-scale fibers possess a range of fiber diameters between 10 nm-10,000 nm.

In some embodiments, the resorbable hybrid-scale fiber matrix wherein the diameters of the hybrid-scale fibers are distributed in a bimodal distributions with at least 25% of fibers possessing a diameter <1000 nm and at least 25% of fibers possessing a diameter >1000 nm.

In some embodiments, the resorbable hybrid-scale fiber matrix wherein the diameters of the hybrid-scale fibers are distributed in a bimodal distributions with at least 10% of fibers possessing a diameter <1000 nm and at least 10% of fibers possessing a diameter >1000 nm.

In some embodiments, the resorbable hybrid-scale fiber matrix wherein the mean pore size is less than 300 $\mu m^2$.

In some embodiments, the resorbable hybrid-scale fiber matrix wherein the porosity of the hybrid-scale fibers . . . and the mean pore size is less than 500 $\mu m^2$.

In some embodiments, the resorbable hybrid-scale fiber matrix wherein the hybrid scale fibers are designed to progressively resorb over time in parallel with tissue regeneration and formation between 4-54 weeks.

In some embodiments, the resorbable hybrid-scale fiber matrix wherein the hybrid scale fibers are designed to progressively resorb over time in parallel with tissue regeneration and formation between 4-100 weeks.

In some embodiments, the resorbable hybrid-scale fiber matrix wherein the wall thickness lies between 250 microns and 550 microns.

In some embodiments, the resorbable hybrid-scale fiber matrix wherein the wall thickness lies between 100 microns and 600 microns.

In some embodiments, the resorbable hybrid-scale fiber matrix wherein the thickness of aligned hybrid-scale fibers lies between 0 to 25% of the total wall thickness.

In some embodiments, the resorbable hybrid-scale fiber matrix wherein the thickness of aligned hybrid-scale fibers lies between 0 to 50% of the total wall thickness.

In some embodiments, the resorbable hybrid-scale fiber matrix wherein the tensile strength should be minimum 10.5N with a mean greater than 15N, suture pullout strength should be minimum 1N with a mean greater than 3N, and compressive strength should be greater than 0.25N without collapsing.

In some embodiments, the resorbable hybrid-scale fiber matrix wherein the tensile strength should be minimum 5N with a mean greater than 10N, suture pullout strength should be minimum 1N with a mean greater than 2N, and compressive strength should be greater than 0.2N without collapsing.

In some embodiments, the resorbable hybrid-scale fiber matrix wherein the uniaxially aligned hybrid are positioned circumferentially or throughout the around the cross-sectional area of the matrix.

In some embodiments, the resorbable hybrid-scale fiber matrix wherein inner diameter is less than 2 microns, and the outer diameter is between 1.5 mm-10 mm In some embodiments, the resorbable hybrid-scale fiber matrix wherein the length of the matrix is 8 mm to 30 mm.

In some embodiments, the resorbable hybrid-scale fiber matrix wherein the length of the matrix is 5 mm to greater than 30 mm.

In some embodiments, the resorbable hybrid-scale fiber matrix wherein the volumetric density of uniaxially aligned fibers is between 0-25%.

In some embodiments, the resorbable hybrid-scale fiber matrix wherein the volumetric density of uniaxially aligned fibers is between 0-50%.

In some embodiments, the resorbable hybrid-scale fiber matrix wherein the volumetric density of uniaxially aligned fibers is low In some embodiments, the resorbable hybrid-scale fiber matrix wherein the volumetric density of uniaxially aligned fibers is medium In some embodiments, the resorbable hybrid-scale fiber matrix wherein the volumetric density of uniaxially aligned fibers is high In some embodiments, the resorbable hybrid-scale fiber matrix wherein the overlap of the outer lumen is between 1-10 mm.

In some embodiments, the resorbable hybrid-scale fiber matrix wherein the matrix is designed to release one or more therapeutically active molecules/biological therapeutics via surface functionalization, bulk loading, physical entrapment, progressive degradation over a defined period of time.

A method for repairing injured nervous tissue by applying the resorbable hybrid-scale fiber matrix to the site of nerve injury.

The method for repairing injured nervous tissue, wherein the injured nerve is identified and surgically exposed or isolated.

The method for repairing injured nervous tissue, wherein the matrix is secured to an injured nerve using one or more techniques including suturing, tissue adhesive, or gravity.

The method for repairing injured nervous tissue, wherein the matrix is applied around the injured nerve tissue.

The method for repairing injured nervous tissue, wherein the matrix is secured end-to-end or in-line with injured nerve tissue.

The method for repairing injured nervous tissue, wherein the matrix supports cellular infiltration, axonal regeneration, elongation, reformation of nervous tissue, and reinnervation of distal nerve segment and end organs.

The method for repairing injured nervous tissue, wherein the matrix completely resorbs via hydrolysis or enzymatic degradation following successful nerve regeneration and functional recovery.

The method for repairing injured nervous tissue, wherein the injured nerve consists of peripheral nerve.

A method for forming a resorbable hybrid-scale fiber matrix for use in facilitating nerve repair and regeneration The method for forming a resorbable hybrid, wherein the method utilizes a solvent consisting of HFIP, DMF, DCM, Acetone, Chloroform, THF, Acetic Acid, Formic Acid, Trifluoroethanol, or Ethyl acetate.

The method for forming a resorbable hybrid, wherein the method involves forming a first tubular structure from at least two or more layers of hybrid-scale fibers.

The method for forming a resorbable hybrid, wherein the method involves cutting the tubular structure to for a wrap or spiral wrap.

The method for forming a resorbable hybrid, wherein the method involves inserting hybrid-scale fibers into the inner lumen/cross sectional area of a first tubular structure.

The method for forming a resorbable hybrid, wherein the method involves rolling a sheet of hybrid-scale fibers into a tubular or spiral structure.

Additional Embodiments

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some examples, the actual steps taken in the processes illustrated and/or disclosed may differ from those shown in the figures. Depending on the example, certain of the steps described above may be removed or others may be added. Furthermore, the features and attributes of the specific examples disclosed above may be combined in different ways to form additional examples, all of which fall within the scope of the present disclosure.

For purposes of this disclosure, certain aspects, advantages, and novel features are described herein. Not necessarily all such advantages may be achieved in accordance with any particular example. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain examples include, while other examples do not include, certain features, elements, and/or steps. Thus, such conditional language is not generally intended to imply that features, elements, and/or steps are in any way required for one or more examples or that one or more examples necessarily include logic for deciding, with or without user input or prompting, whether these features, elements, and/or steps are included or are to be performed in any particular example.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain examples require the presence of at least one of X, at least one of Y, and at least one of Z.

Language of degree used herein, such as the terms "approximately," "about," "generally," and "substantially" represent a value, amount, or characteristic close to the stated value, amount, or characteristic that still performs a desired function or achieves a desired result.

The scope of the present disclosure is not intended to be limited by the specific disclosures of preferred examples in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

Although the foregoing invention has been described in terms of certain preferred embodiments, other embodiments will be apparent to those of ordinary skill in the art. Additionally, other combinations, omissions, substitutions and modification will be apparent to the skilled artisan, in view of the disclosure herein. Accordingly, the present invention is not intended to be limited by the recitation of the preferred embodiments, but is instead to be defined by reference to the appended claims. All references cited herein are incorporated by reference in their entirety.

The terminology used in the description presented herein is not intended to be interpreted in any limited or restrictive manner and unless otherwise indicated refers to the ordinary meaning as would be understood by one of ordinary skill in the art in view of the specification. Furthermore, embodiments may comprise, consist of, consist essentially of, several novel features, no single one of which is solely responsible for its desirable attributes or is believed to be essential to practicing the embodiments herein described. As used herein, the section headings are for organizational purposes only and are not to be construed as limiting the described subject matter in any way. All literature and similar materials cited in this application, including but not limited to, patents, patent applications, articles, books, treatises, and internet web pages are expressly incorporated by reference in their entirety for any purpose. When definitions of terms in incorporated references appear to differ from the definitions provided in the present teachings, the definition provided in the present teachings shall control. It will be appreciated that there is an implied "about" prior to the temperatures, concentrations, times, etc. discussed in the present teachings, such that slight and insubstantial deviations are within the scope of the present teachings herein.

Although this disclosure is in the context of certain embodiments and examples, those of ordinary skill in the art will understand that the present disclosure extends beyond the specifically disclosed embodiments to other alternative embodiments and/or uses of the embodiments and obvious modifications and equivalents thereof. In addition, while several variations of the embodiments have been shown and described in detail, other modifications, which are within the scope of this disclosure, will be readily apparent to those of ordinary skill in the art based upon this disclosure. It is also contemplated that various combinations or sub-combinations of the specific features and aspects of the embodiments may be made and still fall within the scope of the disclosure. It should be understood that various features and aspects of the disclosed embodiments can be combined with, or substituted for, one another in order to form varying modes or embodiments of the disclosure. Thus, it is intended that the scope of the present disclosure herein disclosed should not be limited by the particular disclosed embodiments described above.

The invention claimed is:

1. A resorbable hybrid-scale fiber matrix for use in facilitating nerve repair and regeneration, the matrix comprising:
an inner fiber layer comprising uniaxially-aligned or longitudinally-aligned fibers; and
an outer fiber layer comprising randomly-aligned fibers,
wherein the hybrid-scale fibers comprise fibers having a range of fiber diameters between 10 nm-10,000 nm.

2. A resorbable hybrid-scale fiber matrix for use in facilitating nerve repair and regeneration, the matrix comprising:
an inner fiber layer comprising uniaxially-aligned or longitudinally-aligned fibers; and
an outer fiber layer comprising randomly-aligned fibers,
wherein the diameters of the hybrid-scale fibers are distributed in a bimodal distribution, wherein at least 25% of the fibers possessing a diameter less than 1000 nm and at least 25% of fibers possessing a diameter greater than 1000 nm.

3. The matrix of claim 2, wherein a mean pore size of the matrix is less than 300μ$^2$.

4. A resorbable hybrid-scale fiber matrix for use in facilitating nerve repair and regeneration, the matrix comprising:
an inner fiber layer comprising uniaxially-aligned or longitudinally-aligned fibers; and
an outer fiber layer comprising randomly-aligned fibers,
wherein the fibers are configured to progressively resorb over time in parallel with tissue regeneration and formation between 4-100 weeks.

5. A resorbable hybrid-scale fiber matrix for use in facilitating nerve repair and regeneration the matrix comprising:
an inner fiber layer comprising uniaxially-aligned or longitudinally-aligned fibers; and
an outer fiber layer comprising randomly-aligned fibers,
wherein a total thickness of the inner fiber layer and the outer fiber layer ranges between 250 microns and 550 microns.

6. A resorbable hybrid-scale fiber matrix for use in facilitating nerve repair and regeneration, the matrix comprising:
an inner fiber layer comprising uniaxially-aligned or longitudinally-aligned fibers; and
an outer fiber layer comprising randomly-aligned fibers,
wherein a total thickness of the inner fiber layer and the outer fiber layer ranges between 100 microns and 600 microns,
wherein a mean pore size of the matrix is less than 300μm$^2$.

7. A resorbable hybrid-scale fiber matrix for use in facilitating nerve repair and regeneration, the matrix comprising:
an inner fiber layer comprising uniaxially-aligned or longitudinally-aligned fibers; and
an outer fiber layer comp randomly-aligned fibers,
wherein a thickness of the inner fiber layer ranges between 0 to 50% of the total thickness of both the inner fiber layer and outer fiber layer.

8. A resorbable hybrid-scale fiber matrix for use in facilitating nerve repair and regeneration, the matrix comprising:
an inner fiber layer comprising uniaxially-aligned or longitudinally-aligned fibers; and
an outer fiber layer comprising randomly-aligned fibers,
wherein a tensile strength of the matrix is 10.5 N or more, a suture pullout strength of the matrix is IN or more, and a compressive strength of the matrix is greater than 0.25 N.

9. A resorbable hybrid-scale fiber matrix for use in facilitating nerve repair a regeneration, the matrix comprising;
an inner fiber layer comprising uniaxially-aligned or longitudinally-aligned fibers; and
an outer fiber layer comprising randomly-aligned fibers,
wherein an inner diameter of the inner fiber layer is less than 2 microns, and an outer diameter of the outer fiber layer is between 1.5 mm-10 mm.

10. A resorbable hybrid-scale fiber matrix for use in facilitating nerve repair and regeneration, the matrix comprising;
an inner fiber layer comprising uniaxially-aligned or longitudinally-aligned fibers; and
an outer fiber layer comprising randomly-aligned fibers,
wherein a length of the matrix is 8 mm to 30 mm.

11. A resorbable hybrid-scale fiber matrix for use in facilitating nerve repair and regeneration, the matrix comprising:
an inner fiber layer comprising uniaxially-aligned or longitudinally-aligned fibers; and
an outer fiber layer comprising randomly-aligned fibers,
wherein a length of the matrix is at least 5 mm.

12. A resorbable hybrid-scale fiber matrix for use in facilitating nerve repair and regeneration, the matrix comprising:
   an inner fiber layer comprising uniaxially-aligned or longitudinally-aligned fibers; and
   an outer fiber layer comprising randomly-aligned fibers,
   wherein a volumetric density of uniaxially aligned or longitudinally-aligned fibers is between 0-25%,
   wherein a mean pore size of the matrix is less than 300μm².

13. A resorbable hybrid-scale fiber matrix for use in facilitating nerve repair and regeneration, the matrix comprising:
   an inner fiber comprising uniaxially-aligned or longitudinally-aligned fibers; and
   an outer fiber layer comprising randomly-aligned fibers,
   wherein a volumetric density of uniaxially aligned or longitudinally-aligned fibers is between 0-50%.

14. A resorbable hybrid-scale fiber matrix for use in facilitating nerve repair and regeneration, the matrix comprising:
   an inner fiber layer comprising uniaxially-aligned or longitudinally-aligned fibers; and
   an outer fiber layer comprising randomly-aligned fibers,
   wherein the outer fiber layer comprises an outer lumen contacting an outer surface of the inner fiber layer,
   wherein an overhang defined by the difference in an end of the inner fiber layer and an end of the outer fiber layer is between 1-10 mm.

15. A resorbable hybrid-scale fiber matrix for use in facilitating nerve repair and regeneration, the matrix comprising:
   an inner fiber layer comprising uniaxially-aligned or longitudinally-aligned fibers; and
   an outer fiber layer comprising randomly-aligned fibers,
   wherein the matrix is configured to release one or more therapeutically active molecules or biological therapeutics via one or more of surface functionalization, bulk loading, physical entrapment, or progressive degradation over a defined period of time,
   wherein a mean pore size of the matrix is less than 300μm².

16. The matrix of claim 1, wherein the matrix comprises a shape geometry selected from a group of consisting of a tube, a conduit, a graft, a wrap, or a spiral wrap.

17. The matrix of claim 1, the hybrid-scale fibers comprising a resorbable polymer selected from a group of polymers consisting of polycaprolactone, polylactic acid, polyglycolic acid, polydioxanone, PEO, PEG, poly(3-hydroxybutyrate-co-3-hydroxyvalerate), and combinations thereof.

18. The matrix of claim 1, wherein a mean pore size of the matrix is less than 300μm².

19. The matrix of claim 2, wherein the matrix comprises a shape geometry selected from a group of consisting of a tube, a conduit, a graft, a wrap, or a spiral wrap.

20. The matrix of claim 2, the hybrid-scale fibers comprising a resorbable polymer selected from a group of polymers consisting of polycaprolactone, polylactic acid, polyglycolic acid, polydioxanone, PEO, PEG, poly(3-hydroxybutyrate-co-3-hydroxyvalerate), and combinations thereof.

21. The matrix of claim 2, wherein a mean pore size of the matrix is less than 300μm².

22. The matrix of claim 4, wherein the matrix comprises a shape geometry selected from a group of consisting of a tube, a conduit, a graft, a wrap, or a spiral wrap.

23. The matrix of claim 4, the hybrid-scale fibers comprising a resorbable polymer selected from a group of polymers consisting of polycaprolactone, polylactic acid, polyglycolic acid, polydioxanone, PEO, PEG, poly(3-hydroxybutyrate-co-3-hydroxyvalerate), and combinations thereof.

24. The matrix of claim 4, wherein a mean pore size of the matrix is less than 300μm².

25. The matrix of claim 5, wherein the matrix comprises a shape geometry selected from a group of consisting of a tube, a conduit, a graft, a wrap, or a spiral wrap.

26. The matrix of claim 5, the hybrid-scale fibers comprising a resorbable polymer selected from a group of polymers consisting of polycaprolactone, polylactic acid, polyglycolic acid, polydioxanone, PEO, PEG, poly(3-hydroxybutyrate-co-3-hydroxyvalerate), and combinations thereof.

27. The matrix of claim 5, wherein a mean pore size of the matrix is less than 300μm².

28. The matrix of claim 6, wherein the matrix comprises a shape geometry selected from a group of consisting of a tube, a conduit, a graft, a wrap, or a spiral wrap.

29. The matrix of claim 6, the hybrid-scale fibers comprising a resorbable polymer selected from a group of polymers consisting of polycaprolactone, polylactic acid, polyglycolic acid, polydioxanone, PEO, PEG, poly(3-hydroxybutyrate-co-3-hydroxyvalerate), and combinations thereof.

30. The matrix of claim 7, wherein the matrix comprises a shape geometry selected from a group of consisting of a tube, a conduit, a graft, a wrap, or a spiral wrap.

31. The matrix of claim 7, the hybrid-scale fibers comprising a resorbable polymer selected from a group of polymers consisting of polycaprolactone, polylactic acid, polyglycolic acid, polydioxanone, PEO, PEO, poly(3-hydroxybutyrate-co-3-hydroxyvalerate), and combinations thereof.

32. The matrix of claim 7, wherein a mean pore size of the matrix is less than 300μm².

33. The matrix of claim 8, wherein the matrix comprises a shape geometry selected from a group of consisting of a tube, a conduit, a graft, a wrap, or a spiral wrap.

34. The matrix of claim 8, the hybrid-scale fibers comprising a resorbable polymer selected from a group of polymers consisting of polycaprolactone, polylactic acid, polyglycolic acid, polydioxanone, PEO, PEG, poly(3-hydroxybutyrate-co-3-hydroxyvalerate), and combinations thereof.

35. The matrix of claim 8, wherein a mean pore size of the matrix is less than 300μm².

36. The matrix of claim 9, wherein the matrix comprises a shape geometry selected from a group of consisting of a tube, a conduit, a graft, a wrap, or a spiral wrap.

37. The matrix of claim 9, the hybrid-scale fibers comprising a resorbable polymer selected from a group of polymers consisting of polycaprolactone, polylactic acid, polyglycolic acid, polydioxanone, PEO, PEO, poly(3-hydroxybutyrate-co-3-hydroxyvalerate), and combinations thereof.

38. The matrix of claim 9, wherein a mean pore size of the matrix is less than 300μm².

39. The matrix of claim 10, wherein the matrix comprises a shape geometry selected from a group of consisting of a tube, a conduit, a graft, a wrap, or a spiral wrap.

40. The matrix of claim 10, the hybrid-scale fibers comprising a resorbable polymer selected from a group of polymers consisting of polycaprolactone, polylactic acid, polyglycolic acid, polydioxanone, PEO, PEG, poly(3-hydroxybutyrate-co-3-hydroxyvalerate), and combinations thereof.

41. The matrix of claim 10, wherein a mean pore size of the matrix is less than 300μm².

42. The matrix of claim 11, wherein the matrix comprises a shape geometry selected from a group of consisting of a tube, a conduit, a graft, a wrap, or a spiral wrap.

43. The matrix of claim 11, the hybrid-scale fibers comprising a resorbable polymer selected from a group of polymers consisting of polycaprolactone, polylactic acid, polyglycolic acid, polydioxanone, PEO, PEG, poly(3-hydroxybutyrate-co-3-hydroxyvalerate), and combinations thereof.

44. The matrix of claim 11, wherein a mean pore size of the matrix is less than 300μm².

45. The matrix of claim 12, wherein the matrix comprises a shape geometry selected from a group of consisting of a tube, a conduit, a graft, a wrap, or a spiral wrap.

46. The matrix of claim 12, the hybrid-scale fibers comprising a resorbable polymer selected from a group of polymers consisting of polycaprolactone, polylactic acid, polyglycolic acid, polydioxanone, PEO, PEG, poly(3-hydroxybutyrate-co-3-hydroxyvalerate), and combinations thereof.

47. The matrix of claim 13, wherein the matrix comprises a shape geometry selected from a group of consisting of a tube, a conduit, a graft, a wrap, or a spiral wrap.

48. The matrix of claim 13, the hybrid-scale fibers comprising a resorbable polymer selected from a group of polymers consisting of polycaprolactone, polylactic acid, polyglycolic acid, polydioxanone, PEO, PEG, poly(3-hydroxybutyrate-co-3-hydroxyvalerate), and combinations thereof.

49. The matrix of claim 13, wherein a mean pore size of the matrix is less than 300μm².

50. The matrix of claim 14, wherein the matrix comprises a shape geometry selected from a group of consisting of a tube, a conduit, a graft, a wrap, or a spiral wrap.

51. The matrix of claim 14, the hybrid-scale fibers comprising a resorbable polymer selected from a group of polymers consisting of polycaprolactone, polylactic acid, polyglycolic acid, polydioxanone, PEO, PEG, poly(3-hydroxybutyrate-co-3-hydroxyvalerate), and combinations thereof.

52. The matrix of claim 14, wherein a mean pore size of the matrix is less than 300μm².

53. The matrix of claim 15, wherein the matrix comprises a shape geometry selected from a group of consisting of a tube, a conduit, a graft, a wrap, or a spiral wrap.

54. The matrix of claim 15, the hybrid-scale fibers comprising a resorbable polymer selected from a group of polymers consisting of polycaprolactone, polylactic acid, polyglycolic acid, polydioxanone, PEO, PEG, poly (3-hydroxybutyrate-co-3-hydroxyvalerate), and combinations thereof.

* * * * *